(12) United States Patent
Kase et al.

(10) Patent No.: US 12,221,430 B2
(45) Date of Patent: Feb. 11, 2025

(54) COMPOUND HAVING PYRIMIDINE RING STRUCTURE AND ORGANIC ELECTROLUMINESCENCE DEVICE

(71) Applicant: HODOGAYA CHEMICAL CO., LTD., Tokyo (JP)

(72) Inventors: Kouki Kase, Tokyo (JP); Si-In Kim, Tokyo (JP); Yuta Hirayama, Tokyo (JP); Kazuyuki Suruga, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 411 days.

(21) Appl. No.: 16/646,108

(22) PCT Filed: Sep. 7, 2018

(86) PCT No.: PCT/JP2018/033140
§ 371 (c)(1),
(2) Date: Mar. 10, 2020

(87) PCT Pub. No.: WO2019/049965
PCT Pub. Date: Mar. 14, 2019

(65) Prior Publication Data
US 2020/0277272 A1 Sep. 3, 2020

(30) Foreign Application Priority Data

Sep. 11, 2017 (JP) ................................ 2017-174340

(51) Int. Cl.
*C07D 401/04* (2006.01)
*C07D 401/14* (2006.01)
(Continued)

(52) U.S. Cl.
CPC ......... *C07D 401/04* (2013.01); *C07D 401/14* (2013.01); *C07D 405/14* (2013.01);
(Continued)

(58) Field of Classification Search
CPC .. C07D 401/04; C07D 401/14; C07D 405/14; C07D 409/14; C07D 413/14;
(Continued)

(56) References Cited

U.S. PATENT DOCUMENTS

2006/0154105 A1 7/2006 Yamamoto et al.
2012/0104941 A1 5/2012 Jung et al.
(Continued)

FOREIGN PATENT DOCUMENTS

CN 102471679 A 5/2012
CN 104080882 A 10/2014
(Continued)

OTHER PUBLICATIONS

CA abstract for DE 3319843A1 (Year: 1984).*
Extended European Search Report for European Application No. 18854331.8, dated May 10, 2021.
"Organic LEDs using Hexaphenylbenzene Derivatives", Proceedings of the 50th Meeting of The Japan Society of Applied Physics and Related Societies 28p-A-6, p. 1413 (2003), total of 2 pages.
(Continued)

*Primary Examiner* — Robert H Havlin
*Assistant Examiner* — Frank S. Hou
(74) *Attorney, Agent, or Firm* — Birch, Stewart, Kolasch & Birch, LLP

(57) ABSTRACT

It is an object of the present invention to provide, as a material for organic EL device having high efficiency and high durability, an organic compound having excellent characteristics such as excellent electron injection/transport performance, hole blocking performance, and high stability in a film state, and an organic EL device having high efficiency and high durability, which is obtained by using this compound.

A compound having a pyrimidine ring structure, the compound being represented by the following general formula (1).

(Chem. 1)

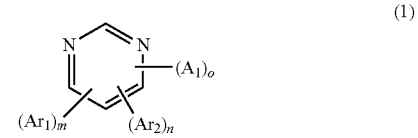

(1)

(In the formula, $A_1$ represents a substituted or unsubstituted aromatic heterocyclic group. $Ar_1$ represents a substituted or unsubstituted aromatic hydrocarbon group, a substituted or unsubstituted aromatic heterocyclic group, or a substituted or unsubstituted fused polycyclic aromatic group. $Ar_2$ represents a deuterium atom, a trimethylsilyl group, a triphenylsilyl group, a substituted or unsubstituted aromatic hydrocarbon group, a substituted or unsubstituted aromatic heterocyclic group, or a substituted or unsubstituted fused polycyclic aromatic group. m represents an integer of 1 to 3, n represents an integer of 0 to 2, and o represents an integer of 1 to 2. In a case where m is an integer of two or more, a plurality of $Ar_1$ bonded to the same pyrimidine ring may be the same or different from each other. In a case where n is an integer of two, a plurality of $Ar_2$ bonded to the same pyrimidine ring may be the same or different from each other. In a case where o is an integer of two, a plurality of $A_1$ bonded to the same pyrimidine ring may be the same or different from each other. However, the sum of the integers of m, n, and o is 4 or less. Note that in a case where n is 0, $Ar_2$ represents a hydrogen atom.)

6 Claims, 12 Drawing Sheets

(51) Int. Cl.
  *C07D 405/14* (2006.01)
  *C07D 409/14* (2006.01)
  *C07D 413/14* (2006.01)
  *C07D 471/04* (2006.01)
  *C07F 7/08* (2006.01)
  *H10K 50/16* (2023.01)
  *H10K 50/17* (2023.01)
  *H10K 85/40* (2023.01)
  *H10K 85/60* (2023.01)

(52) U.S. Cl.
  CPC ......... *C07D 409/14* (2013.01); *C07D 413/14* (2013.01); *C07D 471/04* (2013.01); *C07F 7/0814* (2013.01); *H10K 85/40* (2023.02); *H10K 85/622* (2023.02); *H10K 85/654* (2023.02); *H10K 85/6572* (2023.02); *H10K 85/6574* (2023.02); *H10K 85/6576* (2023.02); *H10K 50/16* (2023.02); *H10K 50/171* (2023.02)

(58) Field of Classification Search
  CPC . C07D 471/04; C07F 7/0814; H01L 51/0054; H01L 51/0067; H01L 51/0072; H01L 51/0073; H01L 51/0074; H01L 51/0094; H01L 51/5072; H01L 51/5092; H01L 51/0058; H01L 51/0052; H01L 51/5096; H01L 51/5012; C09K 11/06; H10K 85/622; H10K 85/654
  See application file for complete search history.

(56) References Cited

U.S. PATENT DOCUMENTS

| | | | |
|---|---|---|---|
| 2014/0018540 A1 | 1/2014 | Sheridan et al. | |
| 2014/0031547 A1 | 1/2014 | Sheridan et al. | |
| 2014/0336392 A1 | 11/2014 | Kim et al. | |
| 2014/0374721 A1 | 12/2014 | Yokoyama et al. | |
| 2015/0209368 A1 | 7/2015 | Sheridan et al. | |
| 2015/0263290 A1 | 9/2015 | Cho et al. | |
| 2016/0058745 A1 | 3/2016 | Sheridan et al. | |
| 2016/0351822 A1* | 12/2016 | Lee | H10K 85/654 |
| 2016/0354375 A1 | 12/2016 | Sheridan et al. | |
| 2017/0170409 A1* | 6/2017 | Xia | H01L 51/0054 |
| 2017/0186967 A1 | 6/2017 | Hayashi et al. | |
| 2017/0200903 A1* | 7/2017 | Park | C09K 11/02 |
| 2020/0168805 A1 | 5/2020 | Park et al. | |
| 2020/0223835 A1 | 7/2020 | Jang et al. | |

FOREIGN PATENT DOCUMENTS

| | | | | |
|---|---|---|---|---|
| CN | 106279103 A | | 1/2017 | |
| CN | 107001321 A | | 8/2017 | |
| CN | 107021926 | * | 8/2017 | ........... C07D 401/10 |
| CN | 107108585 A | | 8/2017 | |
| DE | 3319843 A1 | * | 12/1984 | |
| JP | 8-48656 A | | 2/1996 | |
| JP | 2734341 B2 | | 3/1998 | |
| JP | 33194657 B2 | | 7/2001 | |
| KR | 10-2005-0091080 A | | 9/2005 | |
| KR | 10-2013-0093195 A | | 8/2013 | |
| KR | 10-2013-0142967 A | | 12/2013 | |
| KR | 10-2015-0058625 A | | 5/2015 | |
| KR | 10-2015-0109111 A | | 10/2015 | |
| KR | 10-2015-0117173 A | | 10/2015 | |
| KR | 10-2015-0135626 A | | 12/2015 | |
| KR | 10-2016-0046703 A | | 4/2016 | |
| KR | 10-2016-0082067 A | | 7/2016 | |
| KR | 10-2017-0086211 A | | 7/2017 | |
| KR | 10-2017-0116944 A | | 10/2017 | |
| KR | 10-2019-0009994 A | | 1/2019 | |
| WO | WO 03/060956 A2 | | 7/2003 | |
| WO | WO 2010/074422 A1 | | 7/2010 | |
| WO | WO 2012/023947 A1 | | 2/2012 | |
| WO | WO 2012/080729 A2 | | 6/2012 | |
| WO | WO 2013/054764 A1 | | 4/2013 | |
| WO | WO 2013/085243 A1 | | 6/2013 | |
| WO | WO 2014/009310 A1 | | 1/2014 | |
| WO | WO 2015/190400 A1 | | 12/2015 | |
| WO | WO 2016/064088 A2 | | 4/2016 | |
| WO | WO 2016/089165 A2 | | 6/2016 | |
| WO | WO 2016/108596 A2 | | 7/2016 | |
| WO | WO 2017/043797 A1 | | 3/2017 | |

OTHER PUBLICATIONS

Endo et al., "Efficient up-conversion of triplet excitons into a singlet state and its application for organic light emitting diodes", Applied Physics Letters 98, 083302(2011), total of 3 pages.
Hosokawa et al., "Development of Styryl-Based Light Emitting Material", The Japan Society of Applied Physics, proceedings of the ninth workshop, pp. 55-61 (2001), total of 8 pages.
International Search Report for PCT/JP2018/033140 (PCT/ISA/210) mailed on Nov. 13, 2018.
Kido, "White-Light-Emitting Organic EL Devices", Molecular electronics and bioelectronics, vol. 11, No. 1, pp. 13-19 (2000), total of 10 pages.
Schomaker et al. "Arylation of Halogenated Pyrimidines via a Suzuki Coupling Reaction", J. Org. Chem., vol. 66, No. 21, 2001, pp. 7125-7128.
Wakimoto, "Optimization of driving lifetime durability in organic LED devices using phosphorescent guest emitter", The Japan Society of Applied Physics, proceedings of the ninth workshop, pp. 23-31 (2001), total of 11 pages.
Taiwanese Office Action and Search Report for Taiwanese Application No. 107131849, dated Jan. 10, 2022, with an English translation.
Japanese Office Action for Japanese Application No. 2019-541014, dated Jul. 1, 2022 with English translation.
Taiwanese Office Action and Search Report for Taiwanese Application No. 107131849, dated Jun. 9, 2022, with English translation.
Chinese Office Action and Search Report for Chinese Application No. 201880059472.0, dated Jul. 22, 2022, with a English translation.
Korean Office Action dated Mar. 28, 2023 for Application No. 10-2020-7008115 with an English translation.
Sasada et al., "An Unprecedented Approach to 4,5-Disubstituted Pyrimidine Derivatives by a ZnCl2-Catalyzed Three-Component Coupling Reaction", Organic Letters, vol. 11, No. 10, 2009 (Published on Web Apr. 16, 2009), pp. 2161-2164.
Chinese Office Action for Chinese Application No. 201880059472.0, dated Jan. 13, 2023, with English translation.
Taiwanese Office Action and Search Report for Taiwanese Application No. 107131849, dated Jan. 6, 2023, with English translation.
Chinese Office Action for Chinese Application No. 201880059472.0, dated May 23, 2023, with a English translation.
Taiwanese Office Action and Search Report for Taiwanese Application No. 111138192, dated May 26. 2023, with an English translation.
European Communication pursuant to Article 94(3) EPC for European Application No. 18 854 331.8, dated Jan. 16, 2024.

* cited by examiner

FIG.1

(Compound-1)    (Compound-2)    (Compound-3)

(Compound-4)    (Compound-5)    (Compound-6)

(Compound-7)    (Compound-8)    (Compound-9)

(Compound-10)   (Compound-11)   (Compound-12)

(Compound-13)   (Compound-14)   (Compound-15)

(Compound-31) (Compound-32) (Compound-33)

(Compound-34) (Compound-35) (Compound-36)

(Compound-37) (Compound-38) (Compound-39)

(Compound-40) (Compound-41) (Compound-42)

(Compound-43) (Compound-44) (Compound-45)

FIG.5

(Compound-61) (Compound-62) (Compound-63)

(Compound-64) (Compound-65) (Compound-66)

(Compound-67) (Compound-68) (Compound-69)

(Compound-70) (Compound-71) (Compound-72)

(Compound-73) (Compound-74) (Compound-75)

FIG.6

(Compound-76) (Compound-77) (Compound-78)

(Compound-79) (Compound-80) (Compound-81)

(Compound-82) (Compound-83) (Compound-84)

(Compound-85) (Compound-86) (Compound-87)

(Compound-88) (Compound-89) (Compound-90)

(Compound-106) (Compound-107) (Compound-108)
(Compound-109) (Compound-110) (Compound-111)
(Compound-112) (Compound-113) (Compound-114)
(Compound-115) (Compound-116) (Compound-117)
(Compound-118) (Compound-119) (Compound-120)

US 12,221,430 B2

COMPOUND HAVING PYRIMIDINE RING STRUCTURE AND ORGANIC ELECTROLUMINESCENCE DEVICE

TECHNICAL FIELD

The present invention relates to a compound and a device suitable for an organic electroluminescence device (hereinafter, abbreviated as organic EL device) that is a self-light-emitting device suitable for various display devices, and specifically to a compound having a pyrimidine ring structure and an organic EL device that uses the compound.

BACKGROUND ART

Since the organic EL device is a self-light-emitting device, it is brighter than the liquid crystal device and excellent in visibility, and capable of performing clear display, and thus, active research has been done thereon.

In 1987, C. W. Tang et al. (Eastman Kodak Company) have developed a stacked structural device in which various roles are assigned to the materials, and put an organic EL device using an organic material to practical use. They have stacked a phosphor capable of transporting electrons and an organic material capable of transporting holes, and injected both charges into a phosphor layer to emit light, thereby achieving high luminance of 1000 cd/m$^2$ or more with a voltage of 10 V or less (see, for example, Patent Literature 1 and Patent Literature 2).

Many improvements have been made for practical use of the organic EL device until now. In an electroluminescence device that subdivides the various roles in the stacked structure and includes an anode, a hole injection layer, a hole transport layer, a light-emitting layer, an electron transport layer, an electron injection layer, and a cathode in the stated order on a substrate, high efficiency and durability have been achieved (see, for example, Non-Patent Literature 1).

Further, for the purpose of further improving the light emission efficiency, attempts have been made to use a triplet exciton and utilization of a phosphorescent compound is being considered (see, for example, Non-Patent Literature 2).

Then, a device using light emission by thermally activated delayed fluorescence (TADF) has also been developed. In 2011, Adachi et al. (Kyushu University) have realized the external quantum efficiency of 5.3% by a device using a thermally activated delayed fluorescence material. (see, for example, Non-Patent Literature 3).

The light-emitting layer can also be prepared by doping a charge transport compound generally called a host material with a fluorescent compound, a phosphorescent compound, or a material emitting delayed fluorescence. As described in the above-mentioned Non-Patent Literature, selection of an organic material in the organic EL device significantly affects various properties such as efficiency and durability of the device (see, for example, Non-Patent Literature 2).

In the organic EL device, charges injected from both electrodes are recombined in the light-emitting layer to obtain light emission, and it is important how to efficiently transfer both charges of holes and electrons to the light-emitting layer. For the purpose of this, it is necessary to improve the probability of recombination of holes and electrons in the light-emitting layer by enhancing the electron injection property and enhancing the mobility. Further, by confining the holes transported from the anode side in the light-emitting layer, preventing the electron transport layer from being degraded, and confining the excitons generated in the light-emitting layer, it is possible to create an environment where more recombination can be achieved and achieve highly efficient light emission. Therefore, the role played by the electron transport material is important, and an electron transport material having a high electron injection property, a high mobility of electrons, a high hole blocking property, and a high durability to holes is desired.

Further, from the viewpoint of device lifetime, the heat resistance and amorphous property of the material are also important. In the case of a material having a low heat resistance, thermal decomposition occurs even at a low temperature due to heat generated at the time of driving the device, and the material is degraded. In the case of a material having a low amorphous property, crystallization of the thin film occurs even in a short time, and the device is degraded. Therefore, the material to be used is desired to have a high heat resistance and an excellent amorphous property.

Tris (8-hydroxyquinoline) aluminum (hereinafter, abbreviated as Alq$_3$), which is a typical light-emitting material, is generally used as an electron transport material. However, it cannot be said that the hole blocking property is enough because electron movement in the Alq$_3$ is slow and the work function of the Alq$_3$ is 5.6 eV.

As a compound having improved properties such as the electron injection property and the mobility, a compound having a benzotriazole structure has been proposed (see, for example, Patent Literature 3). However, in the device using these compounds for the electron transport layer, although the light emission efficiency has been improved, it is still not sufficient and a further lower driving voltage and further higher light emission efficiency are desired.

Further, as an electron transport material excellent in the hole blocking property, 3-(4-biphenylyl)-4-phenyl-5-(4-t-butylphenyl)-1,2,4-triazole (hereinafter, abbreviated as TAZ) has been proposed (see, for example, Patent Literature 4).

Because TAZ has a large work function of 6.6 eV and high hole blocking performance, TAZ is used as a hole blocking layer having an electron transport property, which is stacked on the cathode side of a fluorescent light-emitting layer or a phosphorescent light-emitting layer prepared by vacuum deposition, coating, or the like, and contributes to make an organic EL device more highly efficient (see, for example, Non-Patent Literature 4).

However, a low electron transport property has been a major issue in TAZ, and it has been necessary to prepare an organic EL device by combining TAZ with an electron transport material having a higher electron transport property (see, for example, Non-Patent Literature 5).

Further, also in BCP, although the work function is high, i.e., 6.7 eV and the hole blocking performance is high, the stability of the thin film is poor because the glass transition point (Tg) is low, i.e., 83° C., and it cannot be said that BCP sufficiently functions as a hole blocking layer.

None of the materials has sufficient film stability or a sufficient function of blocking holes. In order to improve device properties of an organic EL device, an organic compound that is excellent in electron injection/transport performance and hole blocking performance and has high stability in a film state is desired.

CITATION LIST

Patent Literature

Patent Literature 1: Japanese Patent Application Laid-open No. 1996-048656
Patent Literature 2: Japanese Patent No. 3194657
Patent Literature 3: WO 2013/054764
Patent Literature 4: Japanese Patent Registration No. 2734341
Patent Literature 5: WO 2015/190400
Patent Literature 6: WO 2010/074422
Patent Literature 7: WO 2014/009310
Patent Literature 8: WO 2003/060956

Non-Patent Literature

Non-Patent Literature 1: The Japan Society of Applied Physics, proceedings of the ninth workshop, pp. 55-61 (2001)
Non-Patent Literature 2: The Japan Society of Applied Physics, proceedings of the ninth workshop, pp. 23-31 (2001)
Non-Patent Literature 3: Appl. Phys. Let., 98, 083302(2011)
Non-Patent Literature 4: Proceedings of the 50th Meeting of The Japan Society of Applied Physics and Related Societies 28p-A-6, p. 1413 (2003)
Non-Patent Literature 5: Molecular electronics and bioelectronics, Vol. 11, No. 1, pp. 13-19 (2000)
Non-Patent Literature 6: J. Org. Chem. 2001, 66, 7125-7128

DISCLOSURE OF INVENTION

Technical Problem

It is an object of the present invention to provide, as a material for organic EL device having high efficiency and high durability, an organic compound having excellent characteristics such as excellent electron injection/transport performance, hole blocking performance, and high stability in a film state, and an organic EL device having high efficiency and high durability, which is obtained by using this compound.

Examples of the physical properties that an organic compound to be provided by the present invention should have include (1) having a favorable electron injection property, (2) having high mobility of electrons, (3) being excellent in hole blocking performance, (4) being stable in a film state, and (5) being excellent in the heat resistance. Further, examples of the physical properties that an organic EL device to be provided by the present invention should have include (1) having high light emission efficiency and high power efficiency, (2) having a low light emission start voltage, (3) having a low practical driving voltage, and (4) having a long lifetime.

Solution to Problem

In view of the above, in order to achieve the above-mentioned object, the present inventors have focused on that a nitrogen atom in a pyrimidine ring having electron affinity has the ability to coordinate to metal and excellent heat resistance, designed and chemically synthesized a compound having a pyrimidine ring structure, prototyped various organic EL devices using the compound, and intensively evaluated the properties of the device. As a result, the present invention has been completed.

[1] That is, the present invention is a compound having a pyrimidine ring structure, the compound being represented by the following general formula (1).

(Chem. 1)

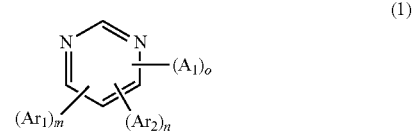

(1)

(In the formula, $A_1$ represents a substituted or unsubstituted aromatic heterocyclic group. $Ar_1$ represents a substituted or unsubstituted aromatic hydrocarbon group, a substituted or unsubstituted aromatic heterocyclic group, or a substituted or unsubstituted fused polycyclic aromatic group. $Ar_2$ represents a deuterium atom, a trimethylsilyl group, a triphenylsilyl group, a substituted or unsubstituted aromatic hydrocarbon group, a substituted or unsubstituted aromatic heterocyclic group, or a substituted or unsubstituted fused polycyclic aromatic group. m represents an integer of 1 to 3, n represents an integer of 0 to 2, and o represents an integer of 1 to 2. In a case where m is an integer of two or more, a plurality of $Ar_1$ bonded to the same pyrimidine ring may be the same or different from each other. In a case where n is an integer of two, a plurality of $Ar_2$ bonded to the same pyrimidine ring may be the same or different from each other. In a case where o is an integer of two, a plurality of $A_1$ bonded to the same pyrimidine ring may be the same or different from each other. However, the sum of the integers of m, n, and o is 4 or less. Note that in a case where n is 0, $Ar_2$ represents a hydrogen atom.)

[2] Further, the present invention is the compound having a pyrimidine ring structure according to [1] above, in which the compound having a pyrimidine ring structure is represented by the following general formula (2).

(Chem. 2)

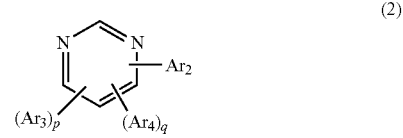

(2)

(In the formula, $A_2$ represents a substituted or unsubstituted aromatic heterocyclic group. $Ar_3$ represents a substituted or unsubstituted aromatic hydrocarbon group, a substituted or unsubstituted aromatic heterocyclic group, or a substituted or unsubstituted fused polycyclic aromatic group. $Ar_4$ represents a deuterium atom, a trimethylsilyl group, a triphenylsilyl group, a substituted or unsubstituted aromatic hydrocarbon group, a substituted or unsubstituted aromatic heterocyclic group, or a substituted or unsubstituted fused polycyclic aromatic group. p represents an integer of 1 to 3, and q represents an integer of 0 to 2. In a case where p is an integer of 2 or more, a plurality of $Ar_3$ bonded to the same pyrimidine ring may be the same or different from each other. In a case where q is an integer of two, a plurality of $Ar_4$ bonded to the same pyrimidine ring may be the same or different from each other. However, the sum of the integers of p and q is 3 or less.)

[3] Further, the present invention is the compound having a pyrimidine ring structure according to [1] above, in which the compound having a pyrimidine ring structure is represented by the following general formula (3).

(Chem. 3)

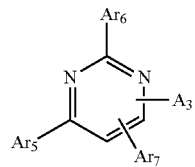

(3)

(In the formula, $A_3$ represents a substituted or unsubstituted aromatic heterocyclic group. $Ar_5$ and $Ar_6$ each represent a substituted or unsubstituted aromatic hydrocarbon group, a substituted or unsubstituted aromatic heterocyclic group, or a substituted or unsubstituted fused polycyclic aromatic group. $Ar_7$ represents a hydrogen atom, a deuterium atom, a trimethylsilyl group, a triphenylsilyl group, a substituted or unsubstituted aromatic hydrocarbon group, a substituted or unsubstituted aromatic heterocyclic group, or a substituted or unsubstituted fused polycyclic aromatic group.)

[4] Further, the present invention is the compound having a pyrimidine ring structure according to [1] above, in which the compound having a pyrimidine ring structure is represented by the following general formula (4).

(Chem. 4)

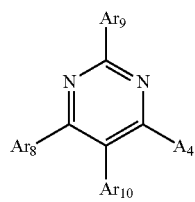

(4)

(In the formula, $A_4$ represents a substituted or unsubstituted aromatic heterocyclic group. $Ar_8$ and $Ar_9$ each represent a substituted or unsubstituted aromatic hydrocarbon group, a substituted or unsubstituted aromatic heterocyclic group, or a substituted or unsubstituted fused polycyclic aromatic group. $Ar_{10}$ represents a hydrogen atom, a deuterium atom, a trimethylsilyl group, a triphenylsilyl group, a substituted or unsubstituted aromatic hydrocarbon group, a substituted or unsubstituted aromatic heterocyclic group, or a substituted or unsubstituted fused polycyclic aromatic group.)

[5] Further, the present invention is the compound having a pyrimidine ring structure according to [1] above, in which the compound having a pyrimidine ring structure is represented by the following general formula (5).

(Chem. 5)

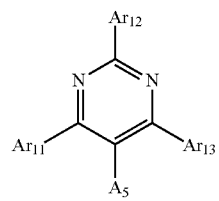

(5)

(In the formula, $A_5$ represents a substituted or unsubstituted aromatic heterocyclic group. $Ar_{11}$ and $Ar_{12}$ each represent a substituted or unsubstituted aromatic hydrocarbon group, a substituted or unsubstituted aromatic heterocyclic group, or a substituted or unsubstituted fused polycyclic aromatic group. $Ar_{13}$ represents a hydrogen atom, a deuterium atom, a trimethylsilyl group, a triphenylsilyl group, a substituted or unsubstituted aromatic hydrocarbon group, a substituted or unsubstituted aromatic heterocyclic group, or a substituted or unsubstituted fused polycyclic aromatic group.)

[6] Further, the present invention is the compound having a pyrimidine ring structure according to [4] above, in which the aromatic heterocyclic group of the $A_4$ is a pyridyl group, a pyrimidyl group, a quinolyl group, an isoquinolyl group, an indolyl group, an azafluorenyl group, a diazafluorenyl group, a quinoxalinyl group, a benzimidazolyl group, a naphthyridinyl group, a phenanthrolinyl group, an acridinyl group, an azaspirobifluorenyl group, a diazaspirobifluorenyl group, or a carbonyl group, the compound having a pyrimidine ring being represented by the general formula (4).

[7] Further, the present invention is the compound having a pyrimidine ring structure according to [5] above, in which the aromatic heterocyclic group of the $A_5$ is a pyridyl group, a pyrimidyl group, a quinolyl group, an isoquinolyl group, an indolyl group, an azafluorenyl group, a diazafluorenyl group, a quinoxalinyl group, a benzimidazolyl group, a naphthyridinyl group, a phenanthrolinyl group, an acridinyl group, an azaspirobifluorenyl group, a diazaspirobifluorenyl group, or a carbonyl group, the compound having a pyrimidine ring structure being represented by the general formula (5).

[8] Further, the present invention is the compound having a pyrimidine ring structure according to according to [4] above, in which the $Ar_{10}$ is a hydrogen atom, the compound having a pyrimidine ring structure being represented by the general formula (4).

[9] Further, the present invention is the compound having a pyrimidine ring structure according to [5] above, in which the $Ar_{13}$ is a hydrogen atom, the compound having a pyrimidine ring structure being represented by the general formula (5).

[10] Further, the present invention is the compound having a pyrimidine ring structure according to [4] above, in which the aromatic heterocyclic group of the $A_4$ is a pyridyl group, a pyrimidyl group, a quinolyl group, an isoquinolyl group, an indolyl group, an azafluorenyl group, a diazafluorenyl group, a quinoxalinyl group, a benzimidazolyl group, a naphthyridinyl group, a phenanthrolinyl group, an acridinyl group, an azaspirobifluorenyl group, a diazaspirobifluorenyl group, or a carbonyl group, and the $Ar_{10}$ is a hydrogen atom, the compound having a pyrimidine ring structure being represented by the general formula (4).

[11] Further, the present invention is the compound having a pyrimidine ring structure according to [5] above, in which the aromatic heterocyclic group of the $A_5$ is a pyridyl group, a pyrimidyl group, a quinolyl group, an isoquinolyl group, an indolyl group, an azafluorenyl group, a diazafluorenyl group, a quinoxalinyl group, a benzimidazolyl group, a naphthyridinyl group, a phenanthrolinyl group, an acridinyl group, an azaspirobifluorenyl group, a diazaspirobifluorenyl group, or a carbonyl group, and the $Ar_{13}$ is a hydrogen atom, the compound having a pyrimidine ring structure being represented by the general formula (5).

[12] Further, the present invention is the compound having a pyrimidine ring structure according to [4] above, in which at least one group in the $Ar_8$ and $Ar_9$ is a phenanthrenyl group, a fluorenyl group, a spirobifluorenyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, or a dibenzothienyl group as a fused polycyclic aromatic group, an aromatic heterocyclic group, or a substituted group, and the $Ar_{10}$ is a hydrogen atom, the compound having a pyrimidine ring structure being represented by the general formula (4).

[13] Further, the present invention is the compound having a pyrimidine ring structure according to [5] above, in which at least one group in the $Ar_{11}$ and $Ar_{12}$ is a phenanthrenyl group, a fluorenyl group, a spirobifluorenyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, or a dibenzothienyl group as a fused polycyclic aromatic group, an aromatic heterocyclic group, or a substituted group, and the $Ar_{13}$ is a hydrogen atom, the compound having a pyrimidine ring structure being represented by the general formula (5).

[14] Further, the present invention is the compound having a pyrimidine ring structure according to [4] above, in which the aromatic heterocyclic group of the $A_4$ is a pyridyl group, a pyrimidyl group, a quinolyl group, an isoquinolyl group, an indolyl group, an azafluorenyl group, a diazafluorenyl group, a quinoxalinyl group, a benzimidazolyl group, a naphthyridinyl group, a phenanthrolinyl group, an acridinyl group, an azaspirobifluorenyl group, a diazaspirobifluorenyl group, or a carbonyl group, the $Ar_{10}$ is a hydrogen atom, and at least one group in the $Ar_8$ and $Ar_9$ is a phenanthrenyl group, a fluorenyl group, a spirobifluorenyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, or a dibenzothienyl group as a fused polycyclic aromatic group, an aromatic heterocyclic group, or a substituted group, the compound having a pyrimidine ring structure being represented by the general formula (4).

[15] Further, the present invention is the compound having a pyrimidine ring structure according to [5] above, in which the aromatic heterocyclic group of the $A_5$ is a pyridyl group, a pyrimidyl group, a quinolyl group, an isoquinolyl group, an indolyl group, an azafluorenyl group, a diazafluorenyl group, a quinoxalinyl group, a benzimidazolyl group, a naphthyridinyl group, a phenanthrolinyl group, an acridinyl group, an azaspirobifluorenyl group, a diazaspirobifluorenyl group, or a carbolinyl group, the $Ar_{13}$ is a hydrogen atom, and at least one group in the $Ar_{11}$ and $Ar_{12}$ is a phenanthrenyl group, a fluorenyl group, a spirobifluorenyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, or a dibenzothienyl group as a fused polycyclic aromatic group, an aromatic heterocyclic group, or a substituted group, the compound having a pyrimidine ring structure being represented by the general formula (5).

[16] Further, the present invention is an organic EL device including a pair of electrodes and at least one organic layer sandwiched between the pair of electrodes, characterized in that the compound having a pyrimidine ring structure according to [1] above is used as a constituent material of the at least one organic material.

[17] Further, the present invention is the organic EL device according to [16] above, in which the organic layer for which the compound having a pyrimidine ring structure is used is an electron transport layer.

[18] Further, the present invention is the organic EL device according to [16] above, in which the organic layer for which the compound having a pyrimidine ring structure is used is a hole blocking layer.

[19] Further, the present invention is the organic EL device according to [16] above, in which the organic layer for which the compound having a pyrimidine ring structure is used is a light-emitting layer.

[20] Further, the present invention is the organic EL device according to [16] above, in which the organic layer for which the compound having a pyrimidine ring structure is used is an electron injection layer.

Advantageous Effects of Invention

A compound having a pyrimidine ring structure according to the present invention has characteristics such as (1) having a favorable electron injection property, (2) having high mobility of electrons, (3) having excellent hole blocking performance, (4) being stable in a film state, and (5) having excellent heat resistance, and an organic EL device according to the present invention has characteristics such as (6) having high light emission efficiency, (7) having a low light emission start voltage, (8) having a low practical driving voltage, and (9) a long lifetime.

BRIEF DESCRIPTION OF DRAWINGS

FIG. 1 is a diagram showing a compound-1 to a compound-15 each having a pyrimidine ring structure according to the present invention.

FIG. 5 is a diagram showing a compound-61 to a compound-75 each having a pyrimidine ring structure according to the present invention.

FIG. 6 is a diagram showing a compound-76 to a compound-90 each having a pyrimidine ring structure according to the present invention.

MODE(S) FOR CARRYING OUT THE INVENTION

Figure 2:
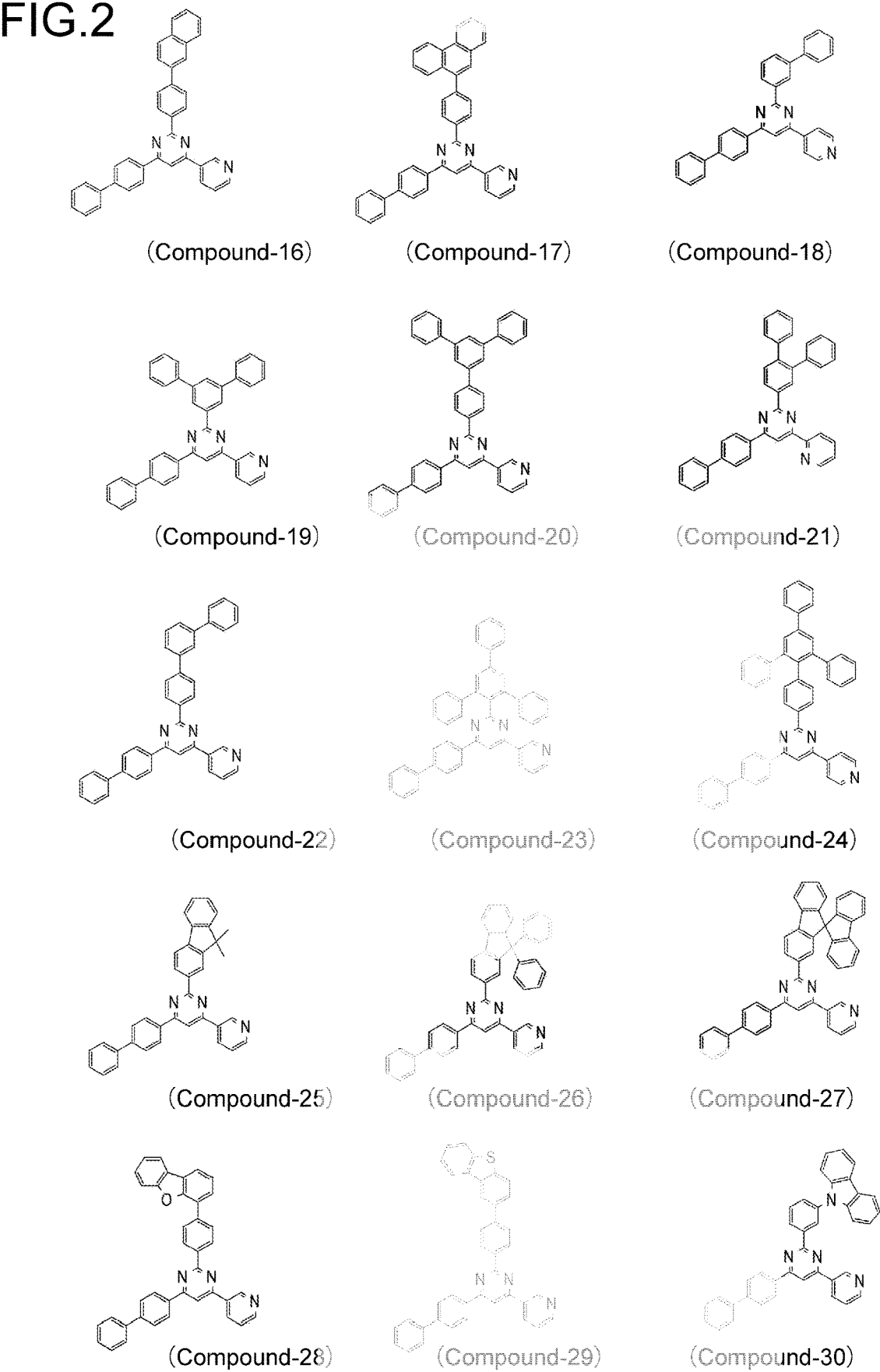
FIG. 2 is a diagram showing a compound-16 to a compound-30 each having a pyrimidine ring structure according to the present invention.
Figure 3:
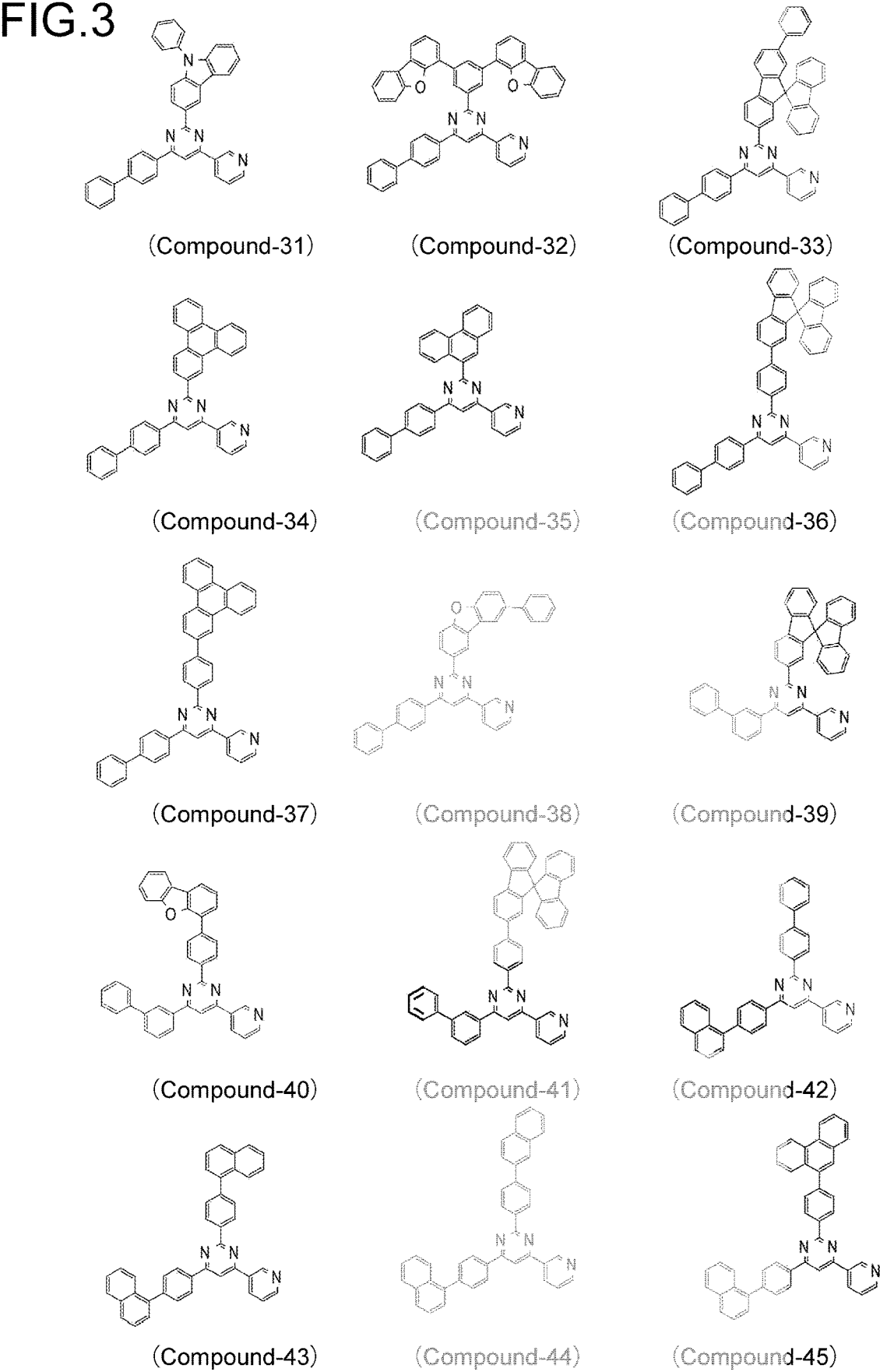
FIG. 3 is a diagram showing a compound-31 to a compound-45 each having a pyrimidine ring structure according to the present invention.
Figure 4:
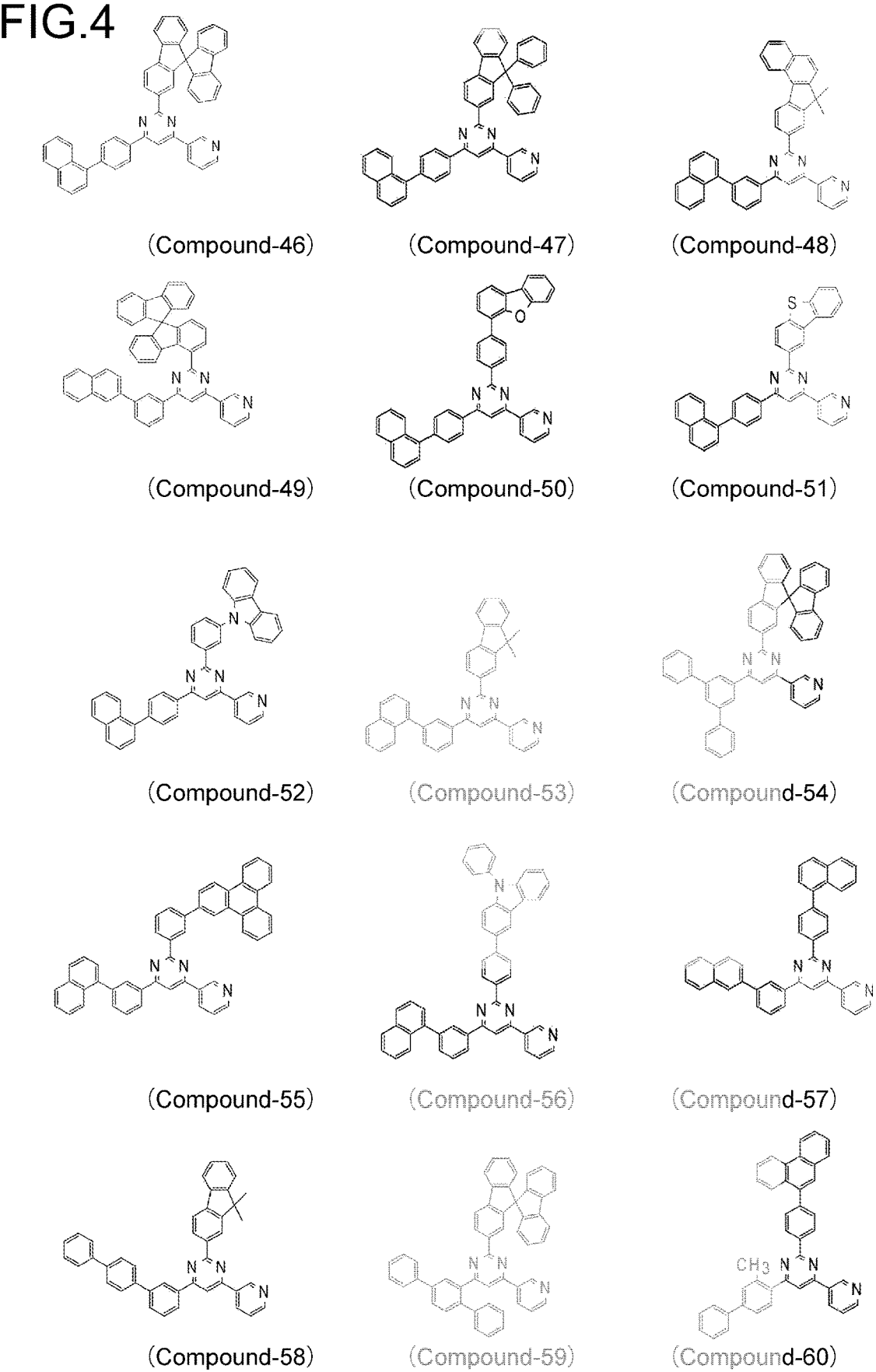
FIG. 4 is a diagram showing a compound-46 to a compound-60 each having a pyrimidine ring structure according to the present invention.
Figure 7:
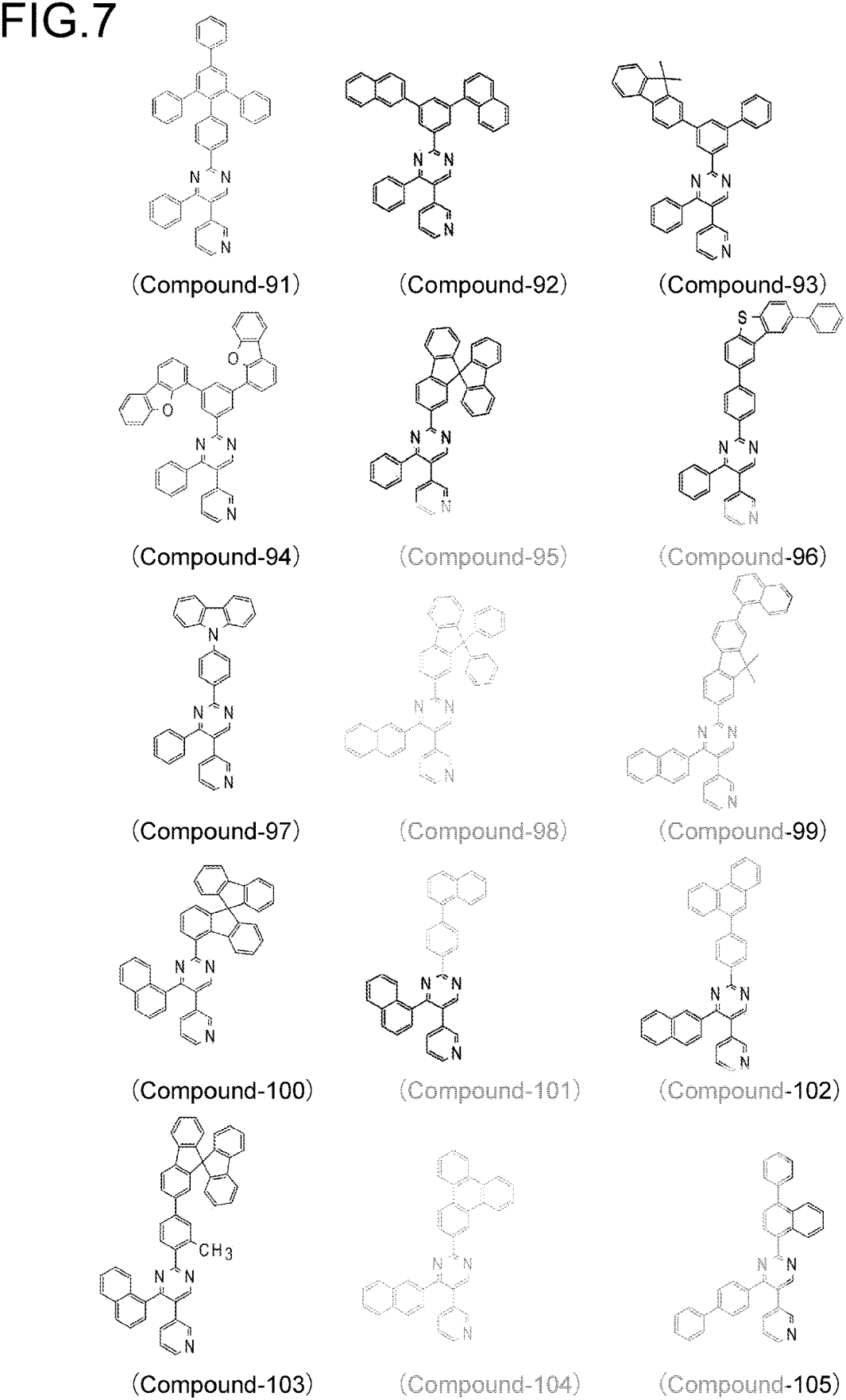
FIG. 7 is a diagram showing a compound-91 to a compound-105 each having a pyrimidine ring structure according to the present invention.
Figure 8:
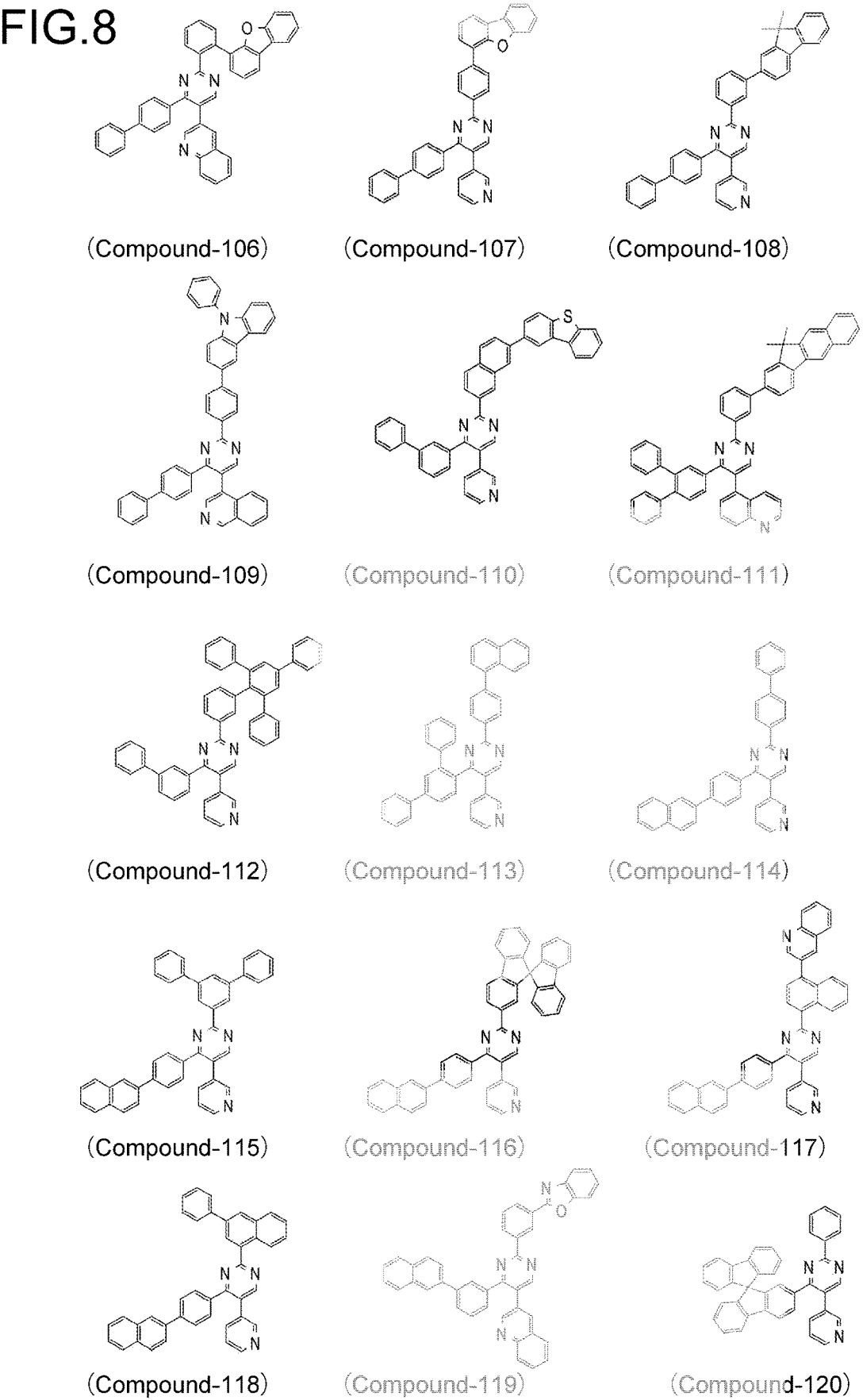
FIG. 8 is a diagram showing a compound-106 to a compound-120 each having a pyrimidine ring structure according to the present invention.
Figure 9:
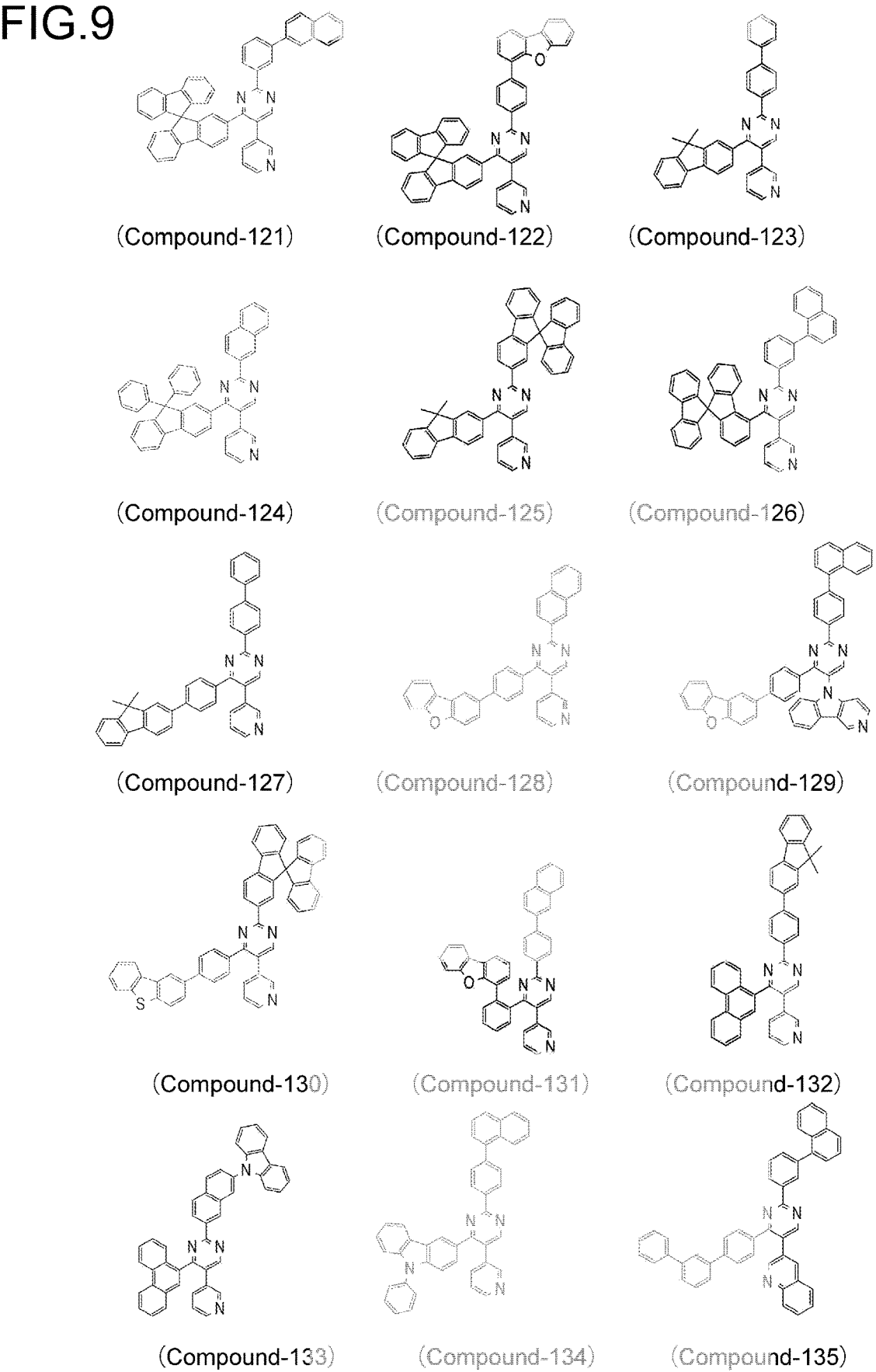
FIG. 9 is a diagram showing a compound-121 to a compound-135 each having a pyrimidine ring structure according to the present invention.
Figure 10:
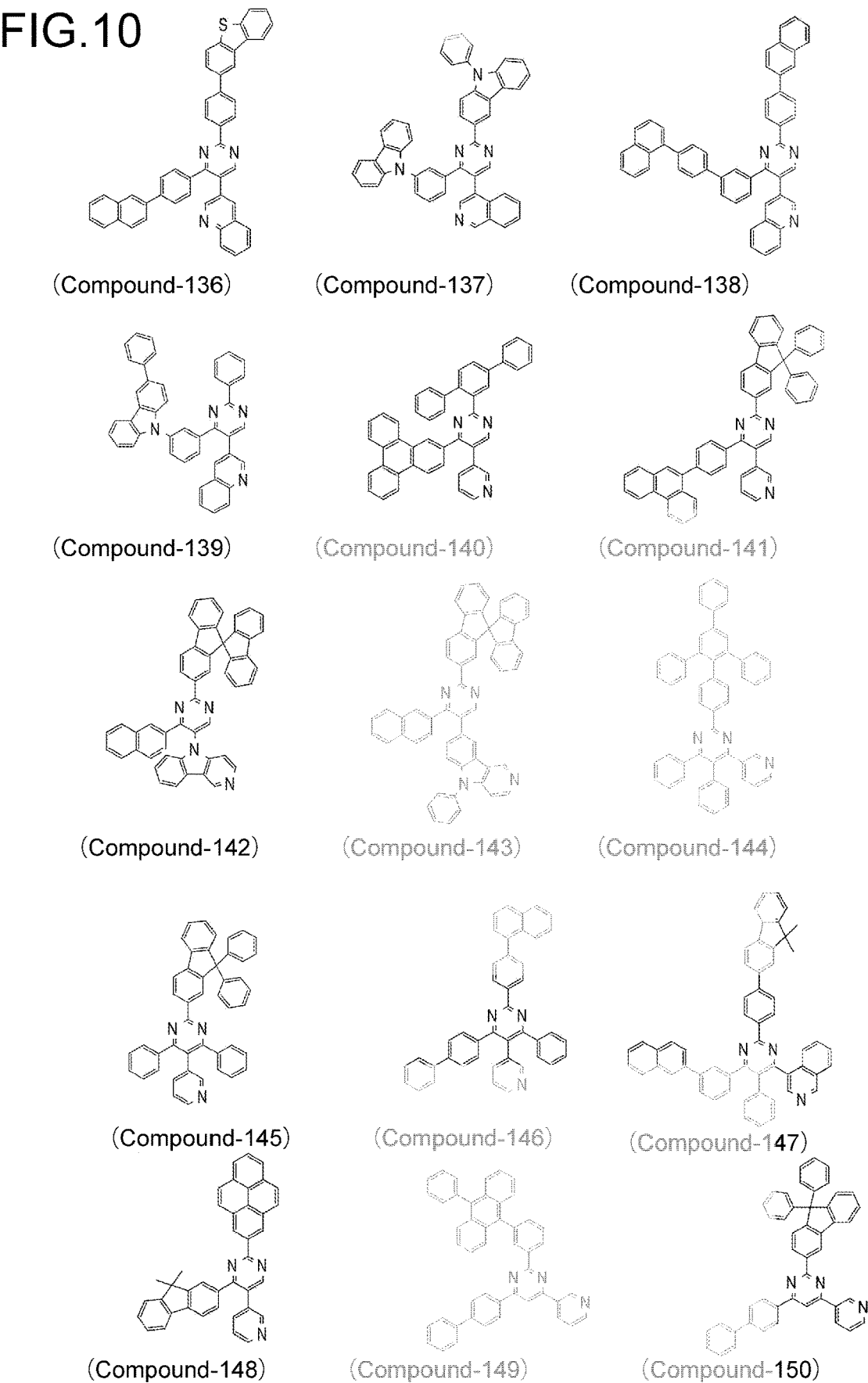
FIG. 10 is a diagram showing a compound-136 to a compound-150 each having a pyrimidine ring structure according to the present invention.
Figure 11:
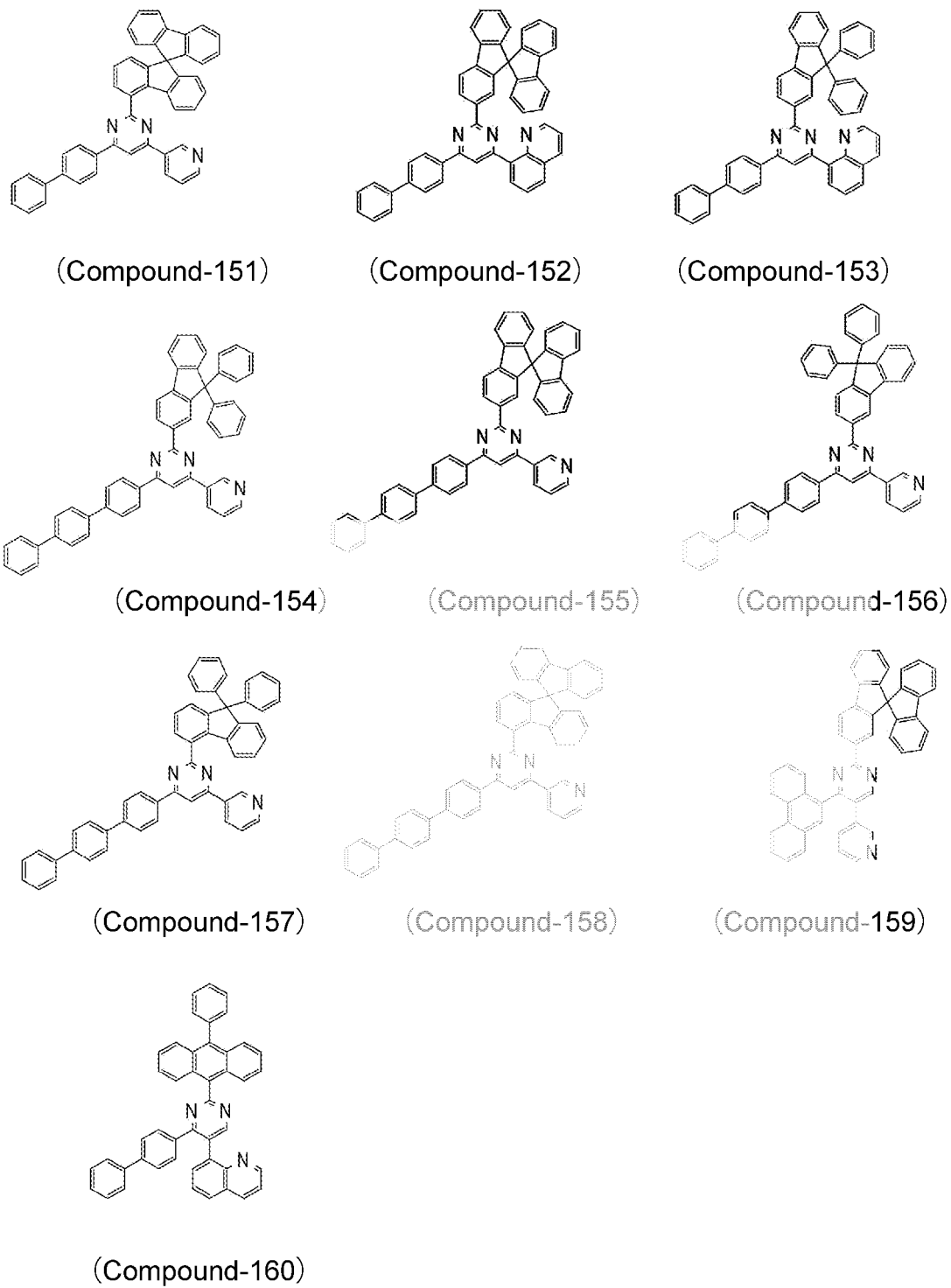
FIG. 11 is a diagram showing a compound-151 to a compound-160 each having a pyrimidine ring structure according to the present invention.

The "aromatic heterocyclic group" in the "substituted or unsubstituted aromatic heterocyclic group" represented by $A_1$ to $A_5$ in the general formulae (1) to (5) is selected from, specifically, the group consisting of a heteroaryl group having 2 to 20 carbon atoms in addition to a pyridyl group, a pyrimidinyl group, a triazinyl group, a furil group, a pyrrolyl group, an imidazolyl group, a thienyl group, a quinolyl group, an isoquinolyl group, a benzofuranyl group, a benzothienyl group, an indolyl group, a carbazolyl group, a benzoxazolyl group, a benzothiazolyl group, an azafluorenyl group, a diazafluorenyl group, an azaspirobifluorenyl group, a diazaspirobifluorenyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group.

The "aromatic hydrocarbon group", "aromatic heterocyclic group", or "fused polycyclic aromatic group" in the "substituted or unsubstituted aromatic hydrocarbon group", "substituted or unsubstituted aromatic heterocyclic group", or "substituted or unsubstituted fused polycyclic aromatic group" represented by $Ar_1$ to $Ar_{13}$ in the general formulae (1) to (5) is selected from, specifically, the group consisting of an aryl group having 6 to 30 carbon atoms and a heteroaryl group having 2 to 20 carbon atoms in addition to a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, a triphenylenyl group, a pyridyl group, a pyrimidinyl group, a triazinyl group, a furil group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, an azafluorenyl group, a diazafluorenyl group, an azaspirobifluorenyl group, a diazaspirobifluorenyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group.

Examples of the "substituted group" in the "substituted aromatic hydrocarbon group", "substituted aromatic heterocyclic group", or "substituted fused polycyclic aromatic group" represented by $A_1$ to $A_5$ and $Ar_1$ to $Ar_{13}$ in the general formulae (1) to (5) include, specifically, a deuterium atom, a cyano group, and a nitro group; a halogen atom such as a fluorine atom, a chlorine atom, a bromine atom, and an iodine atom; a silyl group such as a trimethylsilyl group and a triphenylsilyl group; a linear or branched alkyl group having 1 to 6 carbon atoms such as a methyl group, an ethyl group, and a propyl group; a linear or branched alkyloxy group having 1 to 6 carbon atoms such as a methyloxy group, an ethyloxy group, and a propyloxy group; an alkenyl group such as a vinyl group and an allyl group; an aryloxy group such as a phenyloxy group and a tolyloxy group; an arylalkyloxy group such as a benzyloxy group and a phenethyloxy group; an aromatic hydrocarbon group or fused polycyclic aromatic group such as a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, and a triphenylenyl group; and an aromatic heterocyclic group such as a pyridyl group, a thienyl group, a furil group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group, and these substituted groups may be further substituted with the exemplified substituted groups. Further, benzene rings substituted with these substituted groups or a plurality of substituted groups substituted on the same benzene ring may be bonded to each other via a single bond, a substituted or unsubstituted methylene group, an oxygen atom, or a sulfur atom to form a ring.

A compound having a pyrimidine ring structure represented by the above-mentioned formula (1), which is suitably used for an organic EL device according to the present invention, can be used as a constituent material of an electron injection layer, an electron transport layer, or a hole blocking layer in an organic EL device. This compound is favorable as a material of an electron injection layer or an electron transport layer because it has high mobility of electrons.

Since the organic EL device according to the present invention uses a material for an organic EL device having excellent electron injection/transport performance, stability in a thin film state, and durability, the electron transport efficiency from an electron transport layer to a light-emitting layer is improved, the light emission efficiency is improved, and a drive voltage is reduced as compared with the existing organic EL device, which makes it possible to improve the durability of the organic EL device and realize an organic EL device having high efficiency, a low drive voltage, and a long lifetime.

A compound having a pyrimidine ring structure according to the present invention has characteristics such as (1) having favorable electron injection property, (2) having high mobility of electrons, (3) having excellent hole blocking performance, (4) being stable in a thin film state, and (5) having excellent heat resistance, and an organic EL device according to the present invention has characteristics such as (6) having high light emission efficiency, (7) having a low light emission start voltage, (8) having a low practical driving voltage, and (9) having a long lifetime.

The compound having a pyrimidine ring structure according to the present invention has high electron injection/mobility. Therefore, an organic EL device including an electron injection layer and/or an electron transport layer prepared by using the compound as an electron injection material and/or an electron transport material, the electron transport efficiency to the light-emitting layer is improved, the light emission efficiency is improved, and the drive voltage is reduced, thereby improving the durability of the organic EL device.

The compound having a pyrimidine ring structure according to the present invention is excellent in hole blocking performance and an electron transport property and stable also in a thin film state, and has a feature of confining the excitons generated in the light-emitting layer. Therefore, in an organic EL device including a hole blocking layer prepared by using the compound as a hole blocking property material, the maximum light emission luminance is improved because the probability of recombination of holes and electrons is improved, heat deactivation is suppressed, high light emission efficiency is provided, the drive voltage is reduced, and the current resistance is improved.

The compound having a pyrimidine ring structure according to the present invention has an excellent electron transport property and a wide band gap. Therefore, in an organic EL device including a light-emitting layer prepared by using the compound as a host material, the drive voltage is reduced and the light emission efficiency is improved by forming the light-emitting layer so as to carry a fluorescent material, a phosphorescent material, and a delayed fluorescent material called dopants.

Therefore, the compound having a pyrimidine ring structure according to the present invention is useful as a material of an electron injection layer, an electron transport layer, a hole blocking layer, or a light-emitting layer in an organic EL device, and the light emission efficiency, the drive voltage, and the durability of the existing organic EL device can be improved.

The compound having a pyrimidine ring structure according to the present invention is a novel compound but can be synthesized in accordance with a method well-known per se (see, for example, patent Literature 5, and Non-Patent Literature 6).

As favorable specific examples of a pyrimidine compound represented by the above-mentioned general formula (1) suitably used for the organic EL device according to the present invention, a compound-1 to a compound-160 are shown in FIG. 1 to FIG. 11. However, the present invention is not limited to these compounds.

Purification of compounds represented by the general formulae (1) to (5) each having a pyrimidine ring structure was carried out by purification by column chromatography, adsorption purification with silica gel, activated carbon, activated clay, or the like, recrystallization with a solvent, a crystallization method, a sublimation purification method, or the like. Identification of the compounds was performed by NMR analysis. As physical property values, a melting point, a glass transition point (Tg), and a work function were measured. The melting point is an index of vapor deposition property. The glass transition point (Tg) is an index of stability in a thin film state. The work function is an index of a hole transport property and a hole blocking property.

The melting point and the glass transition point (Tg) were measured with a powder using a high sensitivity differential scanning calorimeter (DSC3100SA manufactured by Bruker AXS GmbH).

The work function was obtained by preparing a thin film of 100 nm on an ITO substrate and using an ionization potential measuring apparatus (PYS-202 manufactured by Sumitomo Heavy Industries, Ltd.).

Examples of the structure of the organic EL device according to the present invention include those including an anode, a hole injection layer, a hole transport layer, a light-emitting layer, an electron transport layer, an electron injection layer, and a cathode in the stated order on a substrate, those including an electron blocking layer between the hole transport layer and the light-emitting layer, and those including a hole blocking layer between the light-emitting layer and the electron transport layer. In the multilayer structures, several organic layers can be omitted or combined. For example, the hole injection layer and the hole transport layer may be combined or the electron injection layer and the electron transport layer may be combined. Further, two or more organic layers having the same function can be stacked. For example, two hole transport layers may be stacked, two light-emitting layers may be stacked, or two electron transport layers may be stacked.

For the anode of the organic EL device according to the present invention, an electrode material having a large work function such as ITO and gold is used. As the hole injection layer of the organic EL device according to the present invention, a starburst type triphenylamine derivative, an arylamine compound having two or more triphenylamine or carbazolyl structures in the molecule, each of which is bonded via a single bond or a divalent group containing no hetero atom, an acceptor heterocyclic compound such as hexacyanoazatriphenylene, a coating type polymer material, or the like in addition to a porphyrin compound typified by copper phthalocyanine can be used. These materials can be formed into a thin film by a known method such as a spin coat method and an ink jet method in addition to a vapor deposition method.

For the hole transport layer of the organic EL device according to the present invention, a benzidine derivative such as N,N'-diphenyl-N,N'-di(m-tolyl)-benzidine (hereinafter, referred to as TPD), N,N'-diphenyl-N,N'-di(a-naphthyl)-benzidine (hereinafter, referred to as NPD), and N,N,N',N'-tetrabiphenylylbenzidine, 1,1-bis[(di-4-tolylamino)phenyl]cyclohexane (hereinafter, referred to as TAPC), an arylamine compound having two or more triphenylamine or carbazolyl structures in the molecule, each of which is bonded via a single bond or a divalent group containing no hetero atom, or the like can be used. These materials may be deposited alone. However, any of the materials may be mixed with another material and used as a single deposited layer. Further, a stacked structure may be achieved by depositing layers of the plurality of materials alone, or mixing the plurality of materials and depositing layers thereof. Alternatively, a stacked structure of at least one layer of any of the plurality of materials deposited alone and at least one layer obtained by mixing the plurality of materials and depositing at least one layer thereof may be achieved. Further, as a hole injection/transport layer, a coating polymer material such as poly(3,4-ethylenedioxythiophene) (hereinafter, referred to as PEDOT)/poly(styrene sulfonate) (hereinafter, referred to as PSS) can be used. These materials can be formed into a thin film by a known method such as a spin coat method and an ink jet method in addition to a vapor deposition method.

Further, for the hole injection layer or hole transport layer, those obtained by P-doping the material typically used for the layer with trisbromophenylamine hexachloroantimony or a radialene derivative (see, for example, Patent Literature 7), a polymer compound having, as a partial structure, the structure of a benzidine derivative such as TPD, or the like can be used.

For the electron blocking layer of the organic EL device according to the present invention, a compound having an electron blocking property, such as a carbazol derivative such as 4,4',4"-tri(N-carbazolyl) triphenylamine (hereinafter, referred to as TCTA), 9,9-bis[4-(carbazol-9-yl)phenyl] fluorene, 1,3-bis(carbazol-9-yl)benzene (hereinafter, referred to as mCP), and 2,2-bis(4-carbazol-9-ylphenyl) adamantane (hereinafter, referred to as Ad-Cz), and a compound having a triphenylsilyl group and a triarylamine structure typified by 9-[4-(carbazol-9-yl)phenyl]-9-[4-(triphenylsilyl)phenyl]-9H-fluorene can be used. These materials may be deposited alone. However, any of the materials may be mixed with another material and used as a single deposited layer. Further, a stacked structure may be achieved by depositing layers of the plurality of materials alone, or mixing the plurality of materials and depositing layers thereof. Alternatively, a stacked structure of at least one layer of any of the plurality of materials deposited alone and at least one layer obtained by mixing the plurality of materials and depositing at least one layer thereof may be achieved. These materials can be formed into a thin film by a known method such as a spin coat method and an ink jet method in addition to a vapor deposition method.

For the light-emitting layer of the organic EL device according to the present invention, a metal complex of a quinolinol derivative including $Alq_3$, various metal complexes, an anthracene derivative a bis-styryl benzene derivative, a pyrene derivative, an oxazole derivative, a poly(p-phenylene vinylene) derivative, or the like in addition to the compound having a pyrimidine ring structure according to the present invention can be used. Further, the light-emitting layer may be formed of a host material and a dopant material. As the host material, an anthracene derivative is favorably used. In addition, not only the above-mentioned light-emitting material including the compound having a pyrimidine ring structure according to the present invention but also a heterocyclic compound having an indole ring as a partial structure of the fused ring, a heterocyclic compound having a carbazol ring as a partial structure of the fused ring, a carbazol derivative, a thiazole derivative, a benzimidazole derivative, a polydialkylfluorene derivative, or the like can be used. Further, as the dopant material, quinacridone, coumarin, rubrene, perylene, and derivatives thereof, a benzopyran derivative, a rhodamine derivative, an aminostyryl derivative, or the like can be used. These materials may be deposited alone. However, any of the materials may be mixed with another material and used as a single deposited layer. Further, a stacked structure may be achieved by depositing layers of the plurality of materials alone, or mixing the plurality of materials and depositing layers thereof. Alternatively, a stacked structure of at least one layer of any of the plurality of materials deposited alone and at least one layer obtained by mixing the plurality of materials and depositing at least one layer thereof may be achieved.

Further, as the light-emitting material, a phosphorescent material can be used. As the phosphorescent material, a phosphorescent material of a metal complex such as iridium and platinum can be used. A green phosphorescent material such as $Ir(ppy)_3$, a blue phosphorescent material such as FIrpic and FIr6, a red phosphorescent material such as $Btp_2Ir$ (acac), or the like is used. As the host material (having a hole injection/transporting property) at this time, the compound having a pyrimidine ring structure according to the present invention in addition to 4,4'-di(N-carbazolyl) biphenyl (hereinafter, referred to as CBP) and a carbazol derivative such as TCTA and mCP can be used. As a host material having an electron transportability, p-bis(triphenylsilyl)benzene (hereinafter, referred to as UGH2), 2,2',2"-(1,3,5-phenylene)-tris(1-phenyl-1H-benzimidazole) (hereinafter, referred to as, TPBI), or the like can be used, and an organic EL device having high performance can be prepared.

In order to avoid concentration quenching, it is favorable to dope the host material with the phosphorescent material by co-deposition in the range of 1 to 30 weight percent with respect to the entire light-emitting layer.

Further, as the light-emitting material, a material emitting delayed fluorescence such as a CDCB derivative including PIC-TRZ, CC2TA, PXZ-TRZ, and 4CzIPN can be used (see, for example, Non-Patent Literature 3). These materials can be formed into a thin film by a known method such as a spin coat method and an ink jet method in addition to a vapor deposition method.

For the hole blocking layer of the organic EL device according to the present invention, a phenanthroline derivative such as bathocuproin (hereinafter, abbreviated as BCP), a compound having a hole blocking effect, such as a metal complex of a quinolinol derivative such as BAlq, various rare earth complexes, an oxazole derivative, a triazole derivative, and a triazine derivative, in addition to the compound having a pyrimidine ring structure according to the present invention, can be used. These materials may double as the material of the electron transport layer. These materials may be deposited alone. However, any of the materials may be mixed with another material and used as a single deposited layer. Further, a stacked structure may be achieved by depositing layers of the plurality of materials alone, or mixing the plurality of materials and depositing layers thereof. Alternatively, a stacked structure of at least one layer of any of the plurality of materials deposited alone and at least one layer obtained by mixing the plurality of materials and depositing at least one layer thereof may be achieved. These materials can be formed into a thin film by a known method such as a spin coat method and an ink jet method in addition to a vapor deposition method.

For the electron transport layer of the organic EL device according to the present invention, a metal complex of a quinolinol derivative including $Alq_3$ and BAlq, various metal complexes, a triazole derivative, a triazine derivative, an oxadiazole derivative, a pyridine derivative, a benzimidazole derivative, a thiadiazole derivative, an anthracene derivative, a carbodiimide derivative, a quinoxaline derivative, a pyridoindole derivative, a phenanthroline derivative, a silole derivative, or the like in addition to the compound having a pyrimidine ring structure according to the present invention can be used. These materials may be deposited alone. However, any of the materials may be mixed with another material and used as a single deposited layer. Further, a stacked structure may be achieved by depositing layers of the plurality of materials alone, or mixing the plurality of materials and depositing layers thereof. Alternatively, a stacked structure of at least one layer of any of the plurality of materials deposited alone and at least one layer obtained by mixing the plurality of materials and depositing at least one layer thereof may be achieved. These materials can be formed into a thin film by a known method such as a spin coat method and an ink jet method in addition to a vapor deposition method.

For the electron injection layer of the organic EL device according to the present invention, an alkali metal salt such as lithium fluoride and cesium fluoride, an alkaline earth metal salt such as magnesium fluoride, a metal complex of a quinolinol derivative such as lithiumquinolinol, a metal oxide such as an aluminum oxide, a metal such as ytterbium (Yb), samarium (Sm), calcium (Ca), strontium (Sr), and cesium (Cs), or the like in addition to the compound having a pyrimidine ring structure according to the present invention can be used. However, this can be omitted in the favorable selection of the electron transport layer and the cathode.

Further, for the electron injection layer or electron transport layer, those obtained by N-doping the material typically used for the layer with a metal such as cesium can be used.

In the cathode of the organic EL device according to the present invention, an electrode material having a low work function, such as aluminum, an alloy having a lower work function, such as a magnesium silver alloy, a magnesium indium alloy, and an aluminum magnesium alloy, or the like is used as the electrode material.

Hereinafter, the embodiment of the present invention will be specifically described by way of Examples. However, the present technology is not limited to the following Examples as long as the essence of the present invention is not exceeded.

Example 1

Synthesis of 6-(biphenyl-4-yl)-2-{4-(phenanthren-9-yl)-phenyl}-4-(pyridin-3-yl)-pyrimidine (Compound-17)

6-(biphenyl-4-yl)-2-chloro-4-(pyridin-3-yl)-pyrimidine: 7.5 g, 4-(phenanthren-9-yl)-phenylboronic acid: 7.2 g, tetrakis (triphenylphosphine) palladium (0): 0.5 g, and potassium carbonate: 6.0 g were charged into a reaction vessel, and stirred under reflux overnight in a mixed solvent of toluene, ethanol and $H_2O$. After the mixture was allowed to cool, an organic layer was extracted by liquid separation and then the extract was concentrated under reduced pressure. The crude product thus obtained was purified by column chromatography (carrier: silica gel, eluent: toluene/ethyl acetate), and thus, a white powder of 6-(biphenyl-4-yl)-2-{4-(phenanthren-9-yl)-phenyl}-4-(pyridin-3-yl)-pyrimidine (Compound-17): 1.5 g (yield of 12%) was obtained.

(Chem. 6)

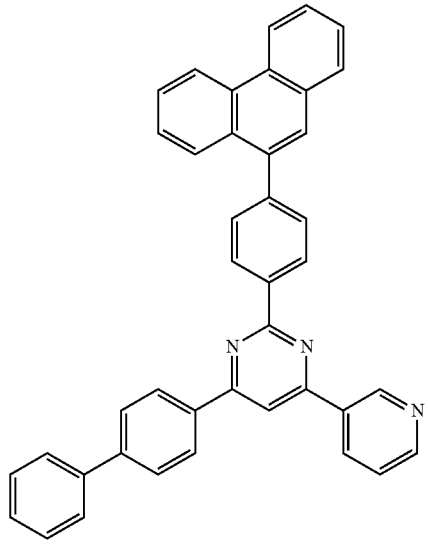

(Compound-17)

The structure of the obtained white powder was identified using NMR.

The following 27 hydrogen signals were detected by 1H-NMR ($CDCl_3$).

δ(ppm)=9.55 (1H), 8.90 (2H), 8.85 (1H), 8.82 (1H), 8.78 (1H), 8.70 (1H), 8.46 (2H), 8.15 (1H), 8.04 (1H), 7.97 (1H), 7.86 (2H), 7.80 (2H), 7.78-7.49 (10H), 7.44 (1H).

Example 2

Synthesis of 6-(biphenyl-4-yl)-2-(9,9-diphenyl [9H] fluoren-2-yl)-4-(pyridin-3-yl)-pyrimidine (Compound-26)

6-(biphenyl-4-yl)-2-chloro-4-(pyridin-3-yl)-pyrimidine: 5.0 g, 2-(9,9-diphenyl [9H] fluorene) boronic acid: 6.8 g, tetrakis (triphenylphosphine) palladium (0): 0.3 g, and potassium carbonate: 2.4 g were charged into a reaction vessel, and stirred under reflux overnight in a mixed solvent of toluene, ethanol and $H_2O$. After the mixture was allowed to cool, an organic layer was extracted by liquid separation and then the extract was concentrated under reduced pressure. The crude product thus obtained was purified by column chromatography (carrier: silica gel, eluent: toluene/ethyl acetate), and thus, a light-gray brown powder of 6-(biphenyl-4-yl)-2-(9,9-diphenyl [9H]fluoren-2-yl)-4-(pyridin-3-yl)-pyrimidine (Compound-26): 6.6 g (yield of 73%) was obtained.

column chromatography (carrier: silica gel, eluent: dichloromethane/ethyl acetate), and thus, a white powder of 6-(biphenyl-4-yl)-4-(pyridin-3-yl)-2-(9,9'-spirobi [9H] fluoren-2-yl)-pyrimidine (Compound-27): 5.5 g (yield of 43%) was obtained.

(Chem. 7)

(Compound-26)

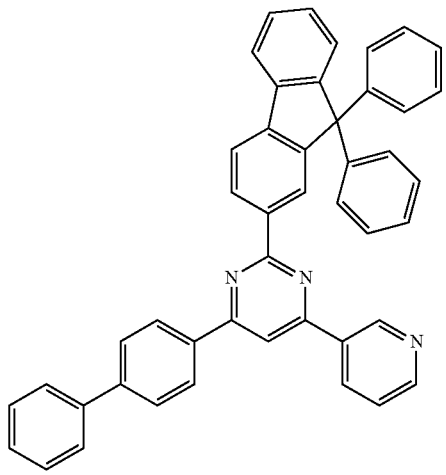

(Chem. 8)

(Compound-27)

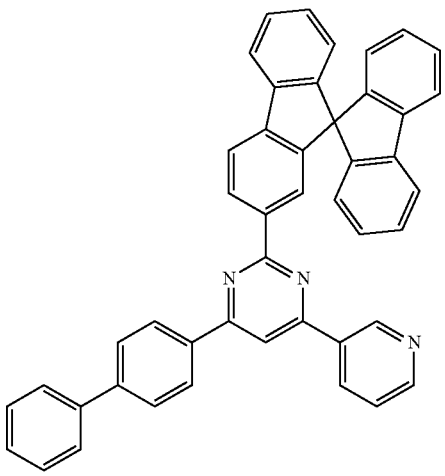

The structure of the obtained light-gray brown powder was identified using NMR.

The following 31 hydrogen signals were detected by $^1$H-NMR (DMSO-$d_6$).

δ(ppm)=9.63 (1H), 8.81 (2H), 8.77 (1H), 8.69 (2H), 8.58 (2H), 8.19 (1H), 8.08 (1H), 7.96 (2H), 7.84 (2H), 7.68 (1H), 7.54 (3H), 7.45 (3H), 7.39-7.21 (10H).

Example 3

<Synthesis of 6-(biphenyl-4-yl)-4-(pyridin-3-yl)-2-(9,9'-spirobi [9H] fluoren-2-yl)-pyrimidine (Compound-27)

6-(biphenyl-4-yl)-2-chloro-4-(pyridin-3-yl)-pyrimidine: 7.0 g, 2-(9,9'-spirobi [9H] fluorene) boronic acid: 8.1 g, tetrakis (triphenylphosphine) palladium (0): 0.5 g, and potassium carbonate: 3.4 g were charged into a reaction vessel, and stirred under reflux overnight in a mixed solvent of toluene, ethanol and H$_2$O. After the mixture was allowed to cool, an organic layer was extracted by liquid separation and then the extract was concentrated under reduced pressure. The crude product thus obtained was purified by The structure of the obtained white powder was identified using NMR.

The following 29 hydrogen signals were detected by $^1$H-NMR (CDCl$_3$).

δ(ppm)=9.37 (1H), 8.85 (1H), 8.75 (1H), 8.46 (1H), 8.26 (2H), 8.06 (1H), 8.05 (1H), 7.94 (4H), 7.77 (2H), 7.69 (2H), 7.55-7.37 (7H), 7.16 (3H), 6.83 (2H), 6.75 (1H).

Example 4

Synthesis of 6-(biphenyl-4-yl)-4-(pyridin-3-yl)-2-{4-(9,9'-spirobi [9H] fluoren-2-yl)-phenyl}-pyrimidine (Compound-36)

By using 4-(9,9'-spirobi [9H] fluoren-2-yl)-phenylboronic acid instead of 2-(9,9'-spirobi [9H]fluorene) boronic acid in Example 3 and performing the reaction under the same conditions, a white powder of 6-(biphenyl-4-yl)-4-(pyridin-3-yl)-2-{4-(9,9'-spirobi [9H] fluoren-2-yl)-phenyl}-pyrimidine (Compound-36): 6.4 g (yield of 45%) was obtained.

(Chem. 9)

(Compound-36)

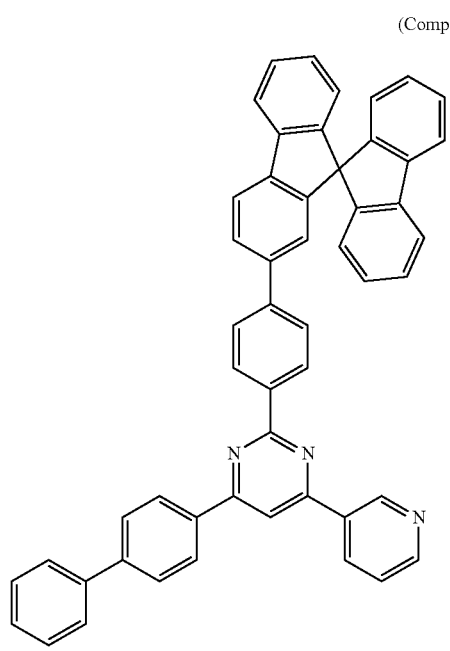

The structure of the obtained white powder was identified using NMR.

The following 33 hydrogen signals were detected by $^1$H-NMR (CDCl$_3$).

δ(ppm)=9.48 (1H), 8.80 (1H), 8.69 (2H), 8.60 (1H), 8.38 (2H), 8.06 (1H), 7.98 (1H), 7.91 (1H), 7.90 (2H), 7.82 (2H), 7.76 (1H), 7.71 (2H), 7.64 (2H), 7.52 (3H), 7.46-7.37 (4H), 7.16 (3H), 7.09 (1H), 6.84 (2H), 6.78 (1H).

Example 5

Synthesis of 2,6-bis{4-(naphthalen-1-yl)-phenyl}-4-(pyridin-3-yl)-pyrimidine (Compound-43)

2-chloro-6-{4-(naphthalen-1-yl)-phenyl}-4-(pyridin-3-yl)-pyrimidine: 8.0 g, 4-(naphthalen-1-yl)-phenylboronic acid: 5.5 g, tetrakis (triphenylphosphine) palladium (0): 0.5 g, and potassium carbonate: 3.4 g were charged into a reaction vessel, and stirred under reflux overnight in a mixed solvent of toluene, ethanol and H$_2$O. After the mixture was allowed to cool, methanol was added to the system, and the precipitated solid was filtered to obtain a crude product. The crude product thus obtained was purified by recrystallization using a monochlorobenzene solvent, and thus, a white powder of 2,6-bis{4-(naphthalen-1-yl)-phenyl}-4-(pyridin-3-yl)-pyrimidine (Compound-43): 6.8 g (yield of 60%) was obtained.

(Chem. 10)

(Compound-43)

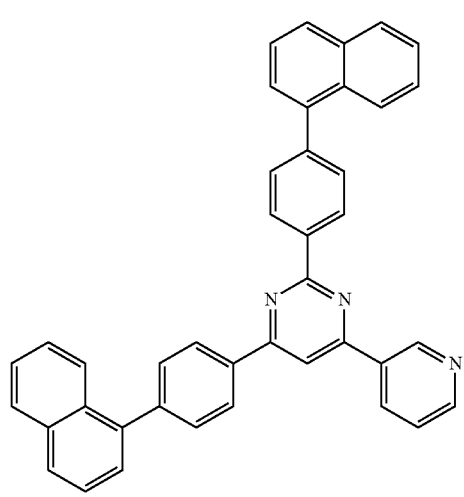

The structure of the obtained white powder was identified using NMR.

The following 27 hydrogen signals were detected by $^1$H-NMR (CDCl$_3$).

δ(ppm)=9.57 (1H), 8.91 (2H), 8.84 (1H), 8.71 (1H), 8.50 (2H), 8.19 (1H), 8.07-7.90 (6H), 7.76 (4H), 7.64-7.45 (9H).

Example 6

Synthesis of 6-{4-(naphthalen-1-yl)-phenyl}-4-(pyridin-3-yl)-2-(9,9'-spirobi [9H] fluoren-2-yl)-pyrimidine (Compound-46)

2-chloro-6-{4-(naphthalen-1-yl)-phenyl}-4-(pyridin-3-yl)-pyrimidine: 8.0 g, 2-(9,9'-spirobi [9H]fluorene) boronic acid: 8.1 g, tetrakis (triphenylphosphine) palladium (0): 0.5 g, and potassium carbonate: 3.4 g were charged into a reaction vessel, and stirred under reflux overnight in a mixed solvent of toluene, ethanol and H$_2$O. After the mixture was allowed to cool, methanol was added to the system, and the precipitated solid was filtered to obtain a crude product. The crude product thus obtained was purified by crystallization using a monochlorobenzene/acetone mixed solvent, and thus, a white powder of 6-{4-(naphthalen-1-yl)-phenyl}-4-(pyridin-3-yl)-2-(9,9'-spirobi [9H] fluoren-2-yl)-pyrimidine (Compound-46): 6.2 g (yield of 45%) was obtained.

(Chem. 11)

(Compound-46)

(Chem. 12)

(Compound-149)

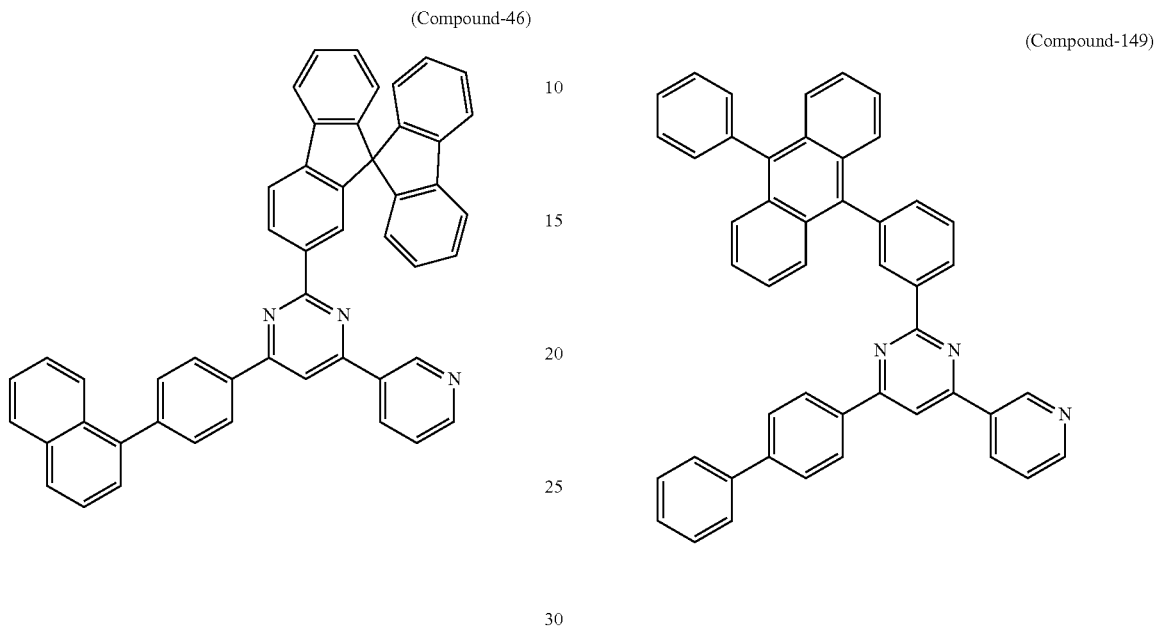

The structure of the obtained white powder was identified using NMR.

The following 31 hydrogen signals were detected by 1H-NMR (CDCl$_3$).

δ(ppm)=9.40 (1H), 8.88 (1H), 8.77 (1H), 8.48 (1H), 8.31 (2H), 8.12-7.87 (9H), 7.68 (2H), 7.57 (2H), 7.53-7.36 (6H), 7.16 (3H), 6.84 (2H), 6.76 (1H).

Example 7

Synthesis of 6-(biphenyl-4-yl)-2-{3-(10-phenyl-anthracen-9-yl)-phenyl}-4-(pyridin-3-yl)-pyrimidine (Compound-149)

6-(biphenyl-4-yl)-2-chloro-4-(pyridin-3-yl)-pyrimidine: 6.0 g, 3-(10-phenyl-anthracen-9-yl) phenylboronic acid: 7.8 g, tetrakis (triphenylphosphine) palladium (0): 0.4 g, and potassium carbonate: 4.8 g were charged into a reaction vessel, and stirred under reflux overnight in a mixed solvent of toluene, ethanol and H$_2$O. After the mixture was allowed to cool, H$_2$O was added to the system, and the precipitated solid was filtered to obtain a crude product. The crude product thus obtained was purified by recrystallization using a monochlorobenzene solvent, and thus, a white powder of 6-(biphenyl-4-yl)-2-{3-(10-phenyl-anthracen-9-yl)-phenyl}-4-(pyridin-3-yl)-pyrimidine (Compound-149): 6.2 g (yield of 56%) was obtained.

The structure of the obtained white powder was identified using NMR.

The following 31 hydrogen signals were detected by 1H-NMR (CDCl$_3$).

δ(ppm)=9.47 (1H), 8.98 (1H), 8.88 (1H), 8.77 (1H), 8.62 (1H), 8.39 (2H), 8.13 (1H), 7.89-7.73 (8H), 7.71-7.34 (15H).

Example 8

Synthesis of 6-(biphenyl-4-yl)-4-(pyridin-3-yl)-2-(9,9'-spirobi [9H] fluorene-4-yl)-pyrimidine (Compound-151)

6-(biphenyl-4-yl)-2-chloro-4-(pyridin-3-yl)-pyrimidine: 5.0 g, 4-(9,9'-spirobi [9H] fluorene) boronic acid: 5.8 g, tetrakis (triphenylphosphine) palladium (0): 0.3 g, and potassium carbonate: 2.4 g were charged into a reaction vessel, and stirred under reflux overnight in a mixed solvent of toluene, ethanol and H$_2$O. After the mixture was allowed to cool, an organic layer was extracted by liquid separation and then the extract was concentrated under reduced pressure. The crude product thus obtained was purified by column chromatography (carrier: silica gel, eluent: toluene), and thus, a light-gray brown powder of 6-(biphenyl-4-yl)-4-(pyridin-3-yl)-2-(9,9'-spirobi [9H]fluorene-4-yl)-pyrimidine (Compound-151): 4.0 g (yield of 44%) was obtained.

(Chem. 13)

(Compound-151)

(Chem. 14)

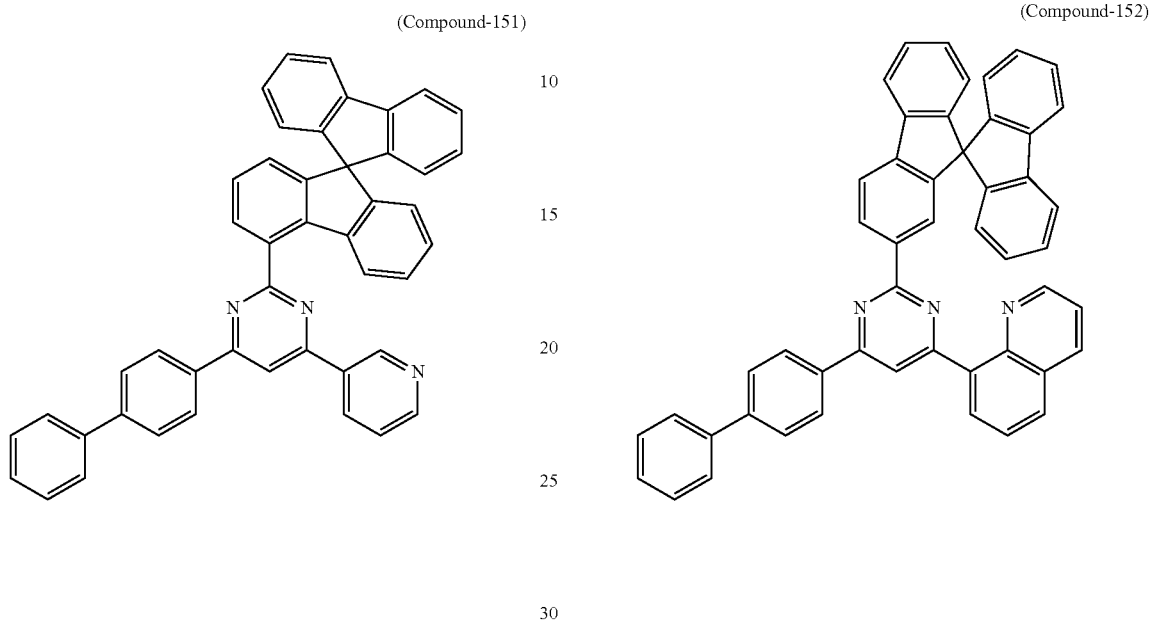

(Compound-152)

The structure of the obtained light-gray brown powder was identified using NMR.

The following 29 hydrogen signals were detected by $^1$H-NMR (DMSO-$d_6$).

δ(ppm)=9.75 (1H), 8.97 (1H), 8.87 (1H), 8.82 (1H), 8.65 (2H), 8.07 (2H), 7.92 (2H), 7.84 (3H), 7.68 (1H), 7.64 (1H), 7.54 (2H), 7.45 (3H), 7.33 (1H), 7.20 (2H), 7.13 (2H), 6.77 (1H), 6.76 (2H), 6.65 (1H).

The structure of the obtained white powder was identified using NMR.

The following 31 hydrogen signals were detected by 1H-NMR (DMSO-$d_6$).

δ(ppm)=8.94 (1H), 8.80 (1H), 8.55 (1H), 8.52 (1H), 8.32 (2H), 8.27 (1H), 8.18 (2H), 8.14 (1H), 8.07 (2H), 7.88 (2H), 7.78 (4H), 7.63 (1H), 7.51 (3H), 7.43 (3H), 7.18 (3H), 6.72 (2H), 6.63 (1H).

Example 9

Synthesis of 6-(biphenyl-4-yl)-4-(quinolin-8-yl)-2-(9,9'-spirobi [9H] fluoren-2-yl)-pyrimidine (Compound-152)

6-(biphenyl-4-yl)-2-chloro-4-(quinolin-8-yl)-pyrimidine: 6.0 g, 2-(9,9'-spirobi [9H] fluorene) boronic acid: 6.0 g, tetrakis (triphenylphosphine) palladium (0): 0.4 g, and potassium carbonate: 2.5 g were charged into a reaction vessel, and stirred under reflux overnight in a mixed solvent of toluene, ethanol and H$_2$O. After the mixture was allowed to cool, methanol was added to the system, and the precipitated solid was filtered to obtain a crude product. The crude product thus obtained was purified by recrystallization using a monochlorobenzene solvent, and thus, a white powder of 6-(biphenyl-4-yl)-4-(quinolin-8-yl)-2-(9,9'-spirobi [9H] fluoren-2-yl)-pyrimidine (Compound-152): 6.5 g (yield of 63%) was obtained.

Example 10

Synthesis of 6-(biphenyl-4-yl)-2-(9,9-diphenyl [9H] fluoren-2-yl)-4-(quinolin-8-yl)-pyrimidine (Compound-153)

6-(biphenyl-4-yl)-2-chloro-4-(quinolin-8-yl)-pyrimidine: 6.0 g, 2-(9,9-diphenyl [9H] fluorene) boronic acid: 7.2 g, tetrakis (triphenylphosphine) palladium (0): 0.4 g, and potassium carbonate: 2.5 g were charged into a reaction vessel, and stirred under reflux overnight in a mixed solvent of toluene, ethanol and H$_2$O. After the mixture was allowed to cool, an organic layer was extracted by liquid separation and then the extract was concentrated under reduced pressure. The crude product thus obtained was purified by recrystallization using an acetone solvent, and thus, a white powder of 6-(biphenyl-4-yl)-2-(9,9-diphenyl [9H] fluoren-2-yl)-4-(quinolin-8-yl)-pyrimidine (Compound-153): 8.5 g (yield of 83%) was obtained.

(Chem. 15)

(Compound-153)

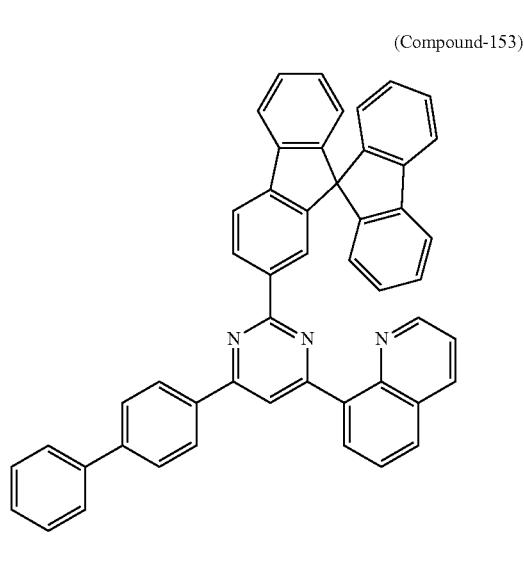

(Chem. 16)

(Compound-154)

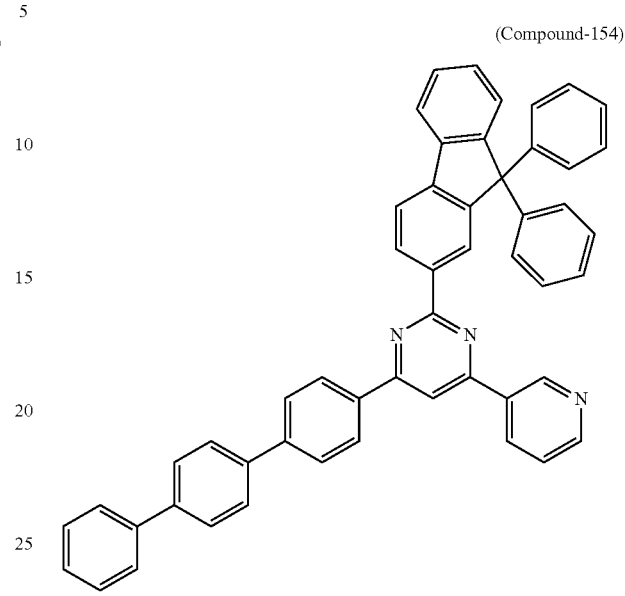

The structure of the obtained white powder was identified using NMR.

The following 33 hydrogen signals were detected by 1H-NMR (CDCl$_3$).

δ(ppm)=9.04 (1H), 8.76 (1H), 8.73 (1H), 8.66 (1H), 8.56 (1H), 8.42 (3H), 8.23 (1H), 8.17 (1H), 8.06 (1H), 7.94 (2H), 7.87 (1H), 7.81 (2H), 7.68 (1H), 7.54 (3H), 7.46 (2H), 7.41 (1H), 7.38-7.19 (10H).

Example 11

Synthesis of 2-(9,9-diphenyl [9H] fluoren-2-yl)-4-(pyridin-3-yl)-6-([1,1';4',1"]terphenyl-4-yl)-pyrimidine (Compound-154)

2-chloro-4-(pyridin-3-yl)-6-([1,1';4',1"]terphenyl-4-yl)-pyrimidine: 8.0 g, 2-(9,9-diphenyl [9H] fluorene) boronic acid: 7.6 g, tetrakis (triphenylphosphine) palladium (0): 0.4 g, and potassium carbonate: 5.4 g were charged into a reaction vessel, and stirred under reflux overnight in a mixed solvent of toluene, ethanol and H$_2$O. After the mixture was allowed to cool, methanol was added to the system, and the precipitated solid was filtered to obtain a crude product. The crude product thus obtained was purified by column chromatography (carrier: silica gel, eluent: dichloromethane/ethyl acetate), and thus, a white powder of 2-(9,9-diphenyl [9H] fluoren-2-yl)-4-(pyridin-3-yl)-6-([1,1';4',1"]terphenyl-4-yl)-pyrimidine (Compound-154): 3.9 g (yield of 29%) was obtained.

The structure of the obtained white powder was identified using NMR.

The following 35 hydrogen signals were detected by $^1$H-NMR (CDCl$_3$).

δ(ppm)=9.47 (1H), 8.81 (1H), 8.80 (2H), 8.57 (1H), 8.37 (2H), 8.05 (1H), 7.96 (1H), 7.88 (3H), 7.78 (4H), 7.68 (2H), 7.56-7.23 (17H).

Example 12

Synthesis of 4-(pyridin-3-yl)-2-(9,9'-spirobi [9H] fluoren-2-yl)-6-([1,1';4',1"]terphenyl-4-yl)-pyrimidine (Compound-155)

2-chloro-4-(pyridin-3-yl)-6-([1,1';4',1"]terphenyl-4-yl)-pyrimidine: 8.0 g, 2-(9,9'-spirobi [9H] fluorene) boronic acid: 6.9 g, tetrakis (triphenylphosphine) palladium (0): 0.4 g, and potassium carbonate: 3.2 g were charged into a reaction vessel, and stirred under reflux overnight in a mixed solvent of toluene, ethanol and H$_2$O. After the mixture was allowed to cool, H$_2$O was added to the system, and the precipitated solid was filtered to obtain a crude product. The crude product thus obtained was purified by column chromatography (carrier: silica gel, eluent: dichloromethane/ethyl acetate), and thus, a white powder of 4-(pyridin-3-yl)-2-(9,9'-spirobi [9H]fluoren-2-yl)-6-([1,1';4',1"]terphenyl-4-yl)-pyrimidine (Compound-155): 4.2 g (yield of 32%) was obtained.

(Chem. 17)

(Compound-155)

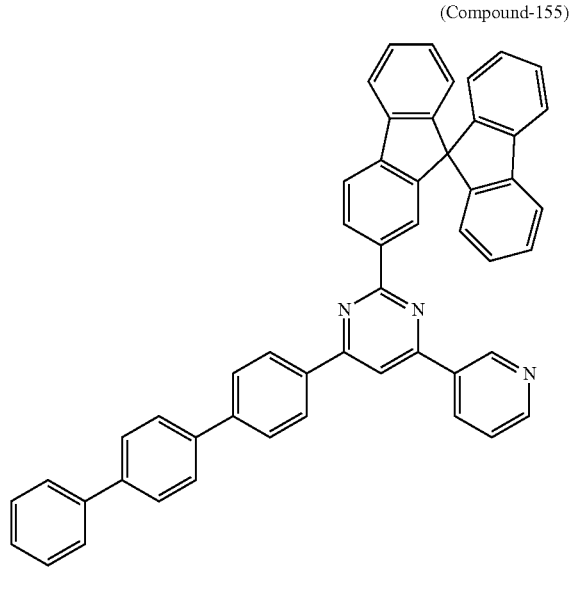

(Chem. 18)

(Compound-156)

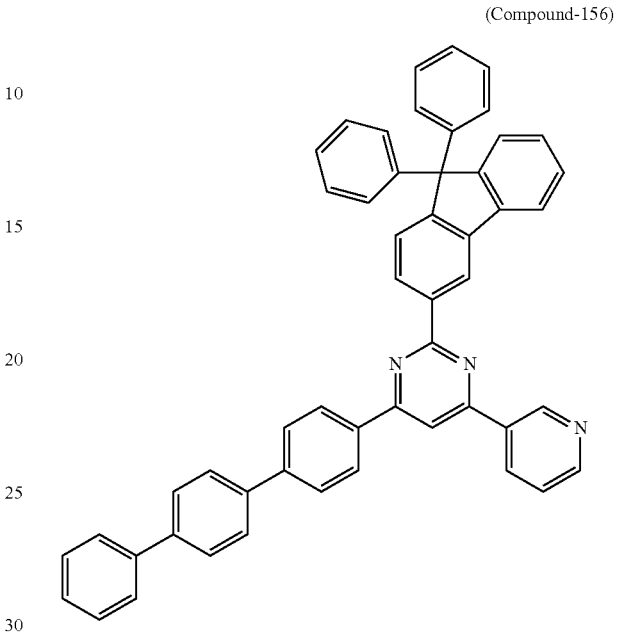

The structure of the obtained white powder was identified using NMR.

The following 33 hydrogen signals were detected by 1H-NMR (CDCl$_3$).

δ(ppm)=9.38 (1H), 8.86 (1H), 8.76 (1H), 8.47 (1H), 8.28 (2H), 8.07 (1H), 8.05 (1H), 7.95 (4H), 7.82 (2H), 7.76 (4H), 7.69 (2H), 7.51 (3H), 7.42 (4H), 7.16 (3H), 6.83 (2H), 6.76 (1H).

Example 13

Synthesis of 2-(9,9-diphenyl [9H] fluorene-3-yl)-4-(pyridin-3-yl)-6-([1,1';4',1' ' ]terphenyl-4-yl)-pyrimidine (Compound-156)

2-chloro-4-(pyridin-3-yl)-6-([1,1';4',1"]terphenyl-4-yl)-pyrimidine: 8.0 g, 3-(9,9-diphenyl [9H] fluorene) boronic acid: 7.6 g, tetrakis (triphenylphosphine) palladium (0): 0.4 g, and potassium carbonate: 5.3 g were charged into a reaction vessel, and stirred under reflux overnight in a mixed solvent of toluene, ethanol and H$_2$O. After the mixture was allowed to cool, H$_2$O was added to the system, and the precipitated solid was filtered to obtain a crude product. The crude product thus obtained was purified by column chromatography (carrier: silica gel, eluent: dichloromethane/ethyl acetate), and thus, a white powder of 2-(9,9-diphenyl [9H] fluorene-3-yl)-4-(pyridin-3-yl)-6-([1,1';4',1"]terphenyl-4-yl)-pyrimidine (Compound-156): 3.4 g (yield of 25%) was obtained.

The structure of the obtained white powder was identified using NMR.

The following 35 hydrogen signals were detected by $^1$H-NMR (CDCl$_3$).

δ(ppm)=9.54 (1H), 9.10 (1H), 8.83 (1H), 8.67 (2H), 8.45 (2H), 8.12 (1H), 8.03 (1H), 7.90 (2H), 7.79 (4H), 7.70 (2H), 7.62 (1H), 7.56 (2H), 7.54-7.23 (15H).

Example 14

Synthesis of 2-(9,9-diphenyl [9H] fluorene-4-yl)-4-(pyridin-3-yl)-6-([1,1';4',1"]terphenyl-4-yl)-pyrimidine (Compound-157)

2-chloro-4-(pyridin-3-yl)-6-([1,1';4',1"]terphenyl-4-yl)-pyrimidine: 5.5 g, 4-(9,9-diphenyl [9H] fluorene) boronic acid: 4.7 g, tetrakis (triphenylphosphine) palladium (0): 0.3 g, and potassium carbonate: 3.6 g were charged into a reaction vessel, and stirred under reflux overnight in a mixed solvent of toluene, ethanol and H$_2$O. After the mixture was allowed to cool, H$_2$O was added to the system, and the precipitated solid was filtered to obtain a crude product. The crude product thus obtained was purified by column chromatography (carrier: silica gel, eluent: dichloromethane/ethyl acetate), and thus, a white powder of 2-(9,9-diphenyl [9H] fluorene-4-yl)-4-(pyridin-3-yl)-6-([1,1';4',1"]terphenyl-4-yl)-pyrimidine (Compound-157): 3.2 g (yield of 35%) was obtained.

(Chem. 19)

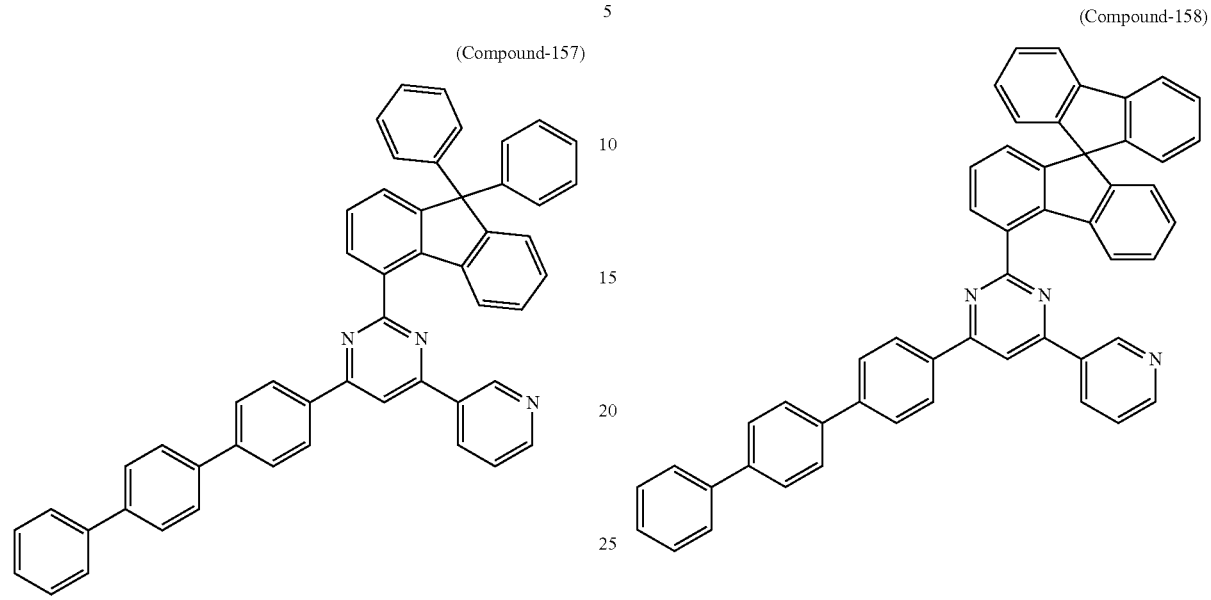

(Compound-157)

The structure of the obtained white powder was identified using NMR.

The following 35 hydrogen signals were detected by $^1$H-NMR (CDCl$_3$).

δ(ppm)=9.50 (1H), 8.81 (1H), 8.64 (1H), 8.43 (2H), 8.30 (1H), 7.86 (3H), 7.77 (4H), 7.68 (2H), 7.60 (1H), 7.58 (1H), 7.54-7.21 (17H), 7.10 (1H).

Example 15

Synthesis of 4-(pyridin-3-yl)-2-(9,9'-spirobi [9H] fluorene-4-yl)-6-([1,1';4',1'']terphenyl-4-yl)-pyrimidine (Compound-158)

2-chloro-4-(pyridin-3-yl)-6-([1,1';4',1'']terphenyl-4-yl)-pyrimidine: 8.0 g, 4-(9,9'-spirobi [9H] fluorene) boronic acid: 6.9 g, tetrakis (triphenylphosphine) palladium (0): 0.4 g, and potassium carbonate: 5.3 g were charged into a reaction vessel, and stirred under reflux overnight in a mixed solvent of toluene, ethanol and H$_2$O. After the mixture was allowed to cool, H$_2$O was added to the system, and the precipitated solid was filtered to obtain a crude product. The crude product thus obtained was purified by column chromatography (carrier: silica gel, eluent: dichloromethane/ethyl acetate), and thus, a white powder of 4-(pyridin-3-yl)-2-(9,9'-spirobi [9H]fluorene-4-yl)-6-([1,1';4',1''] terphenyl-4-yl)-pyrimidine (Compound-158): 3.7 g (yield of 28%) was obtained.

(Chem. 20)

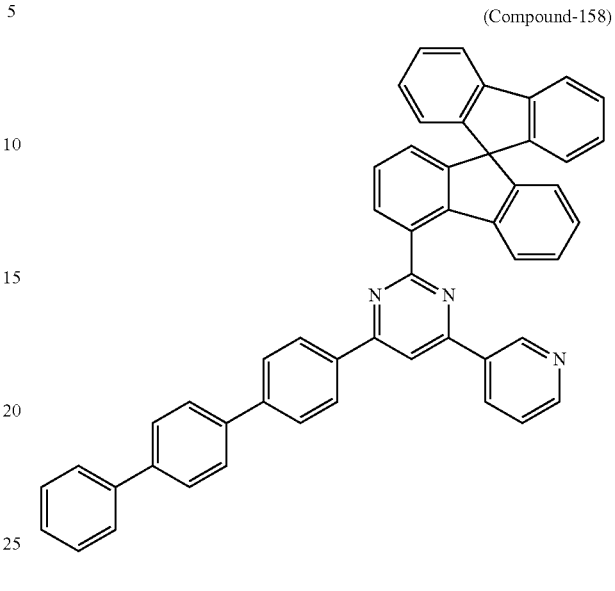

(Compound-158)

The structure of the obtained white powder was identified using NMR.

The following 33 hydrogen signals were detected by 1H-NMR (CDCl$_3$).

δ(ppm)=9.55 (1H), 8.83 (1H), 8.70 (1H), 8.48 (2H), 8.33 (1H), 7.90 (5H), 7.79 (4H), 7.75 (1H), 7.69 (2H), 7.54 (1H), 7.51 (2H), 7.43 (3H), 7.28 (1H), 7.18 (2H), 7.11 (2H), 6.91 (2H), 6.88 (1H), 6.78 (1H).

Example 16

Synthesis of 4-(phenanthren-9-yl)-5-(pyridin-3-yl)-2-(9,9'-spirobi [9H] fluorene-4-yl)-pyrimidine (Compound-159)

5-chloro-4-(phenanthren-9-yl)-2-(9,9'-spirobi [9H]fluorene-4-yl)-pyrimidine: 5.0 g, 3-pyridylboronic acid: 1.2 g, tris(dibenzylideneacetone)dipalladium (0): 0.4 g, tricyclohexylphosphine: 0.5 g, and tripotassium phosphate: 5.3 g were charged into a reaction vessel, and stirred under reflux overnight in a mixed solvent of 1,4-dioxane and H$_2$O. After the mixture was allowed to cool, H$_2$O was added to the system, an organic layer was extracted by liquid separation, and then the extract was concentrated under reduced pressure. The crude product thus obtained was purified by column chromatography (carrier: silica gel, eluent: dichloromethane/ethyl acetate), and thus, a white powder of 4-(phenanthren-9-yl)-5-(pyridin-3-yl)-2-(9,9'-spirobi [9H] fluorene-4-yl)-pyrimidine (Compound-159): 1.7 g (yield of 32%) was obtained.

(Chem. 21)

(Compound-159)

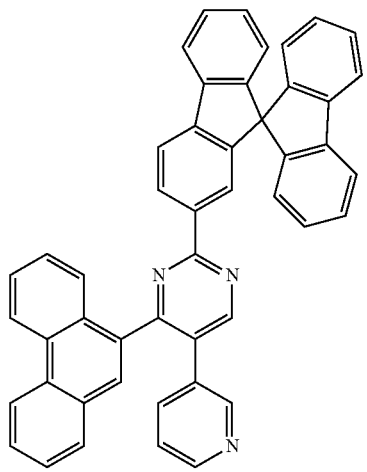

The structure of the obtained white powder was identified using NMR.

The following 29 hydrogen signals were detected by ¹H-NMR (CDCl₃).

δ(ppm)=δ (ppm)=8.84 (1H), 8.70 (2H), 8.67 (1H), 8.47 (1H), 8.33 (1H), 7.98 (1H), 7.96 (1H), 7.91 (1H), 7.87 (2H), 7.78 (1H), 7.70 (1H), 7.61 (4H), 7.46-7.26 (5H), 7.14 (3H), 6.94 (1H), 6.80 (2H), 6.75 (1H).

Example 17

Synthesis of 4-(biphenyl-4-yl)-2-(10-phenyl-anthracen-9-yl)-5-(quinolin-8-yl)-pyrimidine (Compound-160)

4-(biphenyl-4-yl)-5-chloro-2-(10-phenyl-anthracen-9-yl)-pyrimidine: 5.0 g, 8-quinolineboronic acid: 2.0 g, tris(dibenzylideneacetone)dipalladium (0): 0.4 g, tricyclohexylphosphine: 0.5 g, and tripotassium phosphate: 6.1 g were charged into a reaction vessel, and stirred under reflux overnight in a mixed solvent of 1,4-dioxane and H₂O. After the mixture was allowed to cool, H₂O and methanol were added to the system, and the precipitated solid was filtered to obtain a crude product. The crude product thus obtained was purified by crystallization using a toluene/acetone mixed solvent, and thus, a pale yellow powder of 4-(biphenyl-4-yl)-2-(10-phenyl-anthracen-9-yl)-5-(quinolin-8-yl)-pyrimidine (Compound-160): 3.0 g (yield of 51%) was obtained.

(Chem. 22)

(Compound-160)

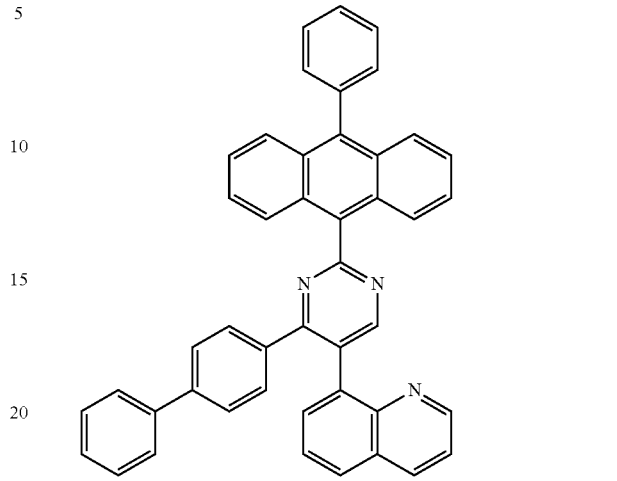

The structure of the obtained pale yellow powder was identified using NMR.

The following 29 hydrogen signals were detected by ¹H-NMR (CDCl₃).

δ(ppm)=9.42 (1H), 9.15 (1H), 8.70 (1H), 8.14 (1H), 7.90 (2H), 7.88-7.59 (10H), 7.55-7.30 (13H).

Example 18

The melting point and the glass transition point of the pyrimidine compound represented by the general formula (1) were measured using a high sensitivity differential scanning calorimeter (DSC3100SA manufactured by Bruker AXS GmbH).

Melting Point Glass Transition Point

| | | |
|---|---|---|
| Compound of Example 1 | 236° C. | 115° C. |
| Compound of Example 2 | 267° C. | 135° C. |
| Compound of Example 3 | Not observed | 146° C. |
| Compound of Example 4 | 331° C. | 164° C. |
| Compound of Example 5 | 257° C. | 103° C. |
| Compound of Example 6 | 306° C. | 157° C. |
| Compound of Example 7 | 303° C. | 144° C. |
| Compound of Example 8 | Not observed | 148° C. |
| Compound of Example 9 | 306° C. | 151° C. |
| Compound of Example 10 | Not observed | 137° C. |
| Compound of Example 11 | 282° C. | 147° C. |
| Compound of Example 12 | 274° C. | 159° C. |
| Compound of Example 13 | 326° C. | 149° C. |
| Compound of Example 14 | 275° C. | 148° C. |
| Compound of Example 15 | Not observed | 161° C. |
| Compound of Example 16 | Not observed | 164° C. |
| Compound of Example 17 | Not observed | 141° C. |

The compound having a pyrimidine ring structure represented by the general formula (1) has the glass transition point of 100° C. or more, which shows that the thin film state is stable.

Example 19

The compound having a pyrimidine ring structure represented by the general formula (1) was used to prepare a vapor deposition film having a film thickness of 100 nm on an ITO substrate, and the work function thereof was measured by an ionization potential measuring apparatus (PYS-202 manufactured by Sumitomo Heavy Industries, Ltd.).

Work Function

| Compound of Example 1 | 6.53 eV |
|---|---|
| Compound of Example 2 | 6.57 eV |
| Compound of Example 3 | 6.52 eV |
| Compound of Example 4 | 6.40 eV |
| Compound of Example 5 | 6.49 eV |
| Compound of Example 6 | 6.53 eV |
| Compound of Example 7 | 5.97 eV |
| Compound of Example 8 | 6.43 eV |
| Compound of Example 9 | 6.51 eV |
| Compound of Example 10 | 6.51 eV |
| Compound of Example 11 | 6.59 eV |
| Compound of Example 12 | 6.58 eV |
| Compound of Example 13 | 6.58 eV |
| Compound of Example 14 | 6.51 eV |
| Compound of Example 15 | 6.56 eV |
| Compound of Example 16 | 6.59 eV |
| Compound of Example 17 | 6.07 eV |

The compound having a pyrimidine ring structure represented by the general formula (1) has a value of work function larger than 5.5 eV that is a value of work function of a general hole transport material such as NPD and TPD and has large hole blocking performance.

Example 20

Figure 12:
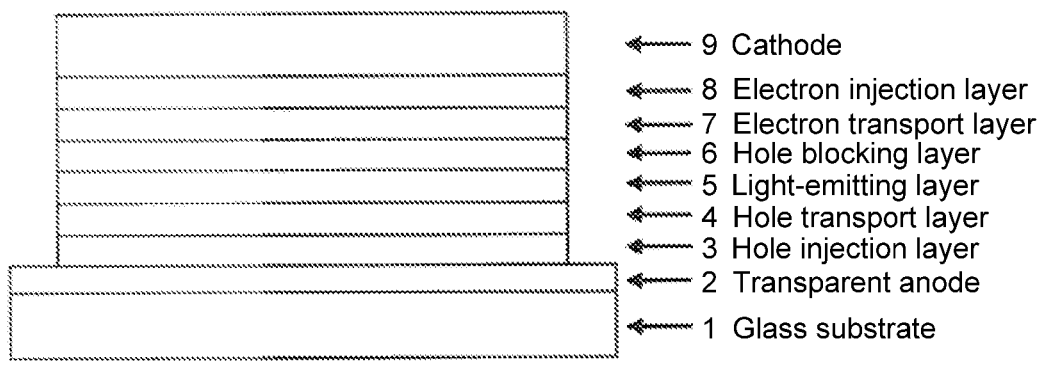
FIG. 12 is a diagram showing a configuration of each of organic EL devices according to Examples 20 to 36 and Comparative Examples 1 and 2.

The organic EL device was prepared by depositing a hole injection layer 3, a hole transport layer 4, a light-emitting layer 5, a hole blocking layer 6, an electron transport layer 7, an electron injection layer 8, and a cathode (aluminum electrode) 9 in the stated order on a transparent anode 2, which has been formed on a glass substrate 1 as an ITO electrode in advance, as shown in FIG. 12.

Specifically, after performing, in isopropyl alcohol for 20 minutes, ultrasonic cleaning on the glass substrate 1 on which ITO having a film thickness of 50 nm was formed, the glass substrate 1 was dried for 10 minutes on a hot plate heated to 200° C. After that, UV ozone treatment was performed for 15 minutes, and then, the ITO-attached glass substrate was mounted in a vacuum deposition machine. The pressure in the vacuum deposition machine was reduced to 0.001 Pa or less. Subsequently, a film of an electron acceptor (Acceptor-1) having the following structural formula and a compound (HTM-1) having the following structural formula was formed, as the hole injection layer 3, to have a film thickness of 10 nm and cover the transparent anode 2 by binary deposition at a deposition rate in which the ratio of the deposition rates of Acceptor-1 and the compound (HTM-1) was 3:97. As the hole transport layer 4, a film of the compound (HTM-1) having the following structural formula was formed on the hole injection layer 3 to have a film thickness of 60 nm. A film of a compound (EMD-1) having the following structural formula and a compound (EMH-1) having the following structural formula was formed, as the light-emitting layer 5, on the hole transport layer 4 to have a film thickness of 20 nm by binary deposition at a deposition rate in which the ratio of the deposition rates of EMD-1 and EMH-1 was 5:95. A film of the compound (Compound-17) according to Example 1 of the present invention and a compound (ETM-1) having the following structural formula was formed on the light-emitting layer 5, as the hole blocking layer and electron transport layer 6 and 7 to have a film thickness of 30 nm by binary deposition at a deposition rate in which the ratio of the deposition rates of the compound (Compound-17) and the compound (ETM-1)

was 50:50. A film of lithium fluoride was formed, as the electron injection layer 8, on the hole blocking layer and electron transport layer 6 and 7 to have a film thickness of 1 nm. Finally, aluminum was deposited to have a thickness of 100 nm to form the cathode 9. The characteristics of the prepared organic EL device were measured at room temperature in the atmosphere. The measurement results of the light-emitting characteristics when a direct current voltage was applied to the prepared organic EL device were collectively shown in Table 1.

(Chem. 23)

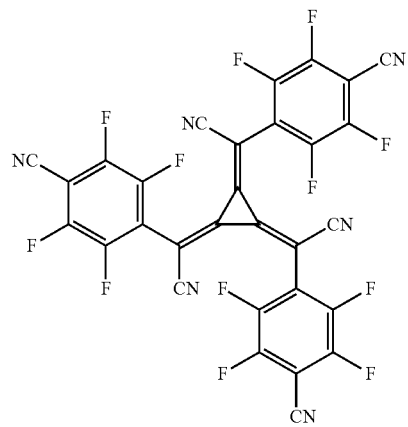

(Acceptor-1)

(Chem. 24)

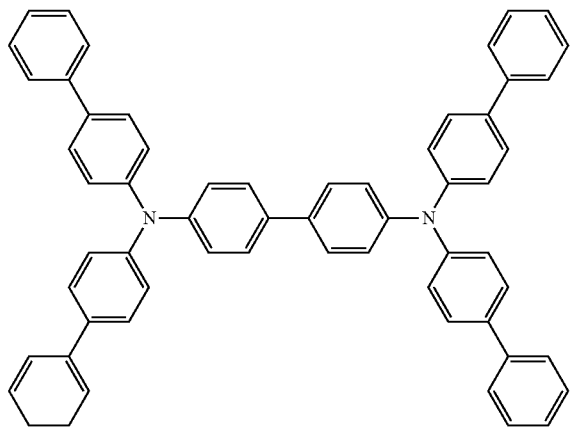

(HTM-1)

(Chem. 25)

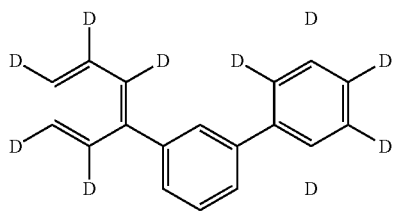

(EMD-1)

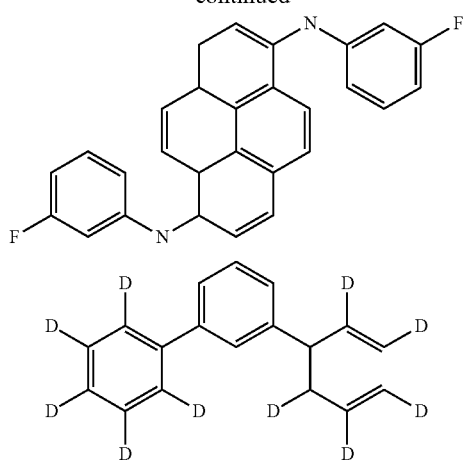

(Chem. 26)

(EMH-1)

(Chem. 27)

(Compound-17)

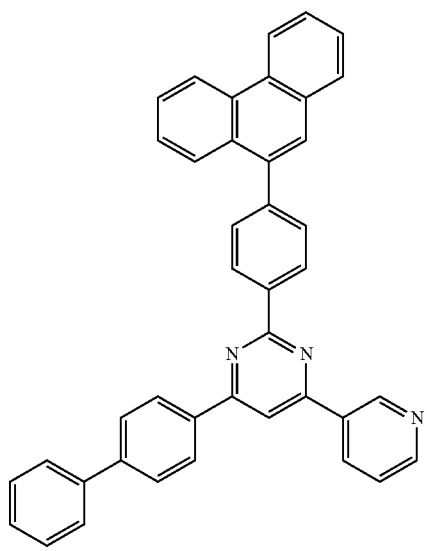

(Chem. 28)

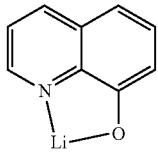

(ETM-1)

Example 21

An organic EL device was prepared in similar conditions to Example 20 except that the compound (Compound 26) according to Example 2 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-26) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 29)

(Compound-26)

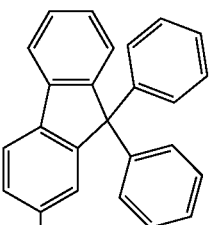

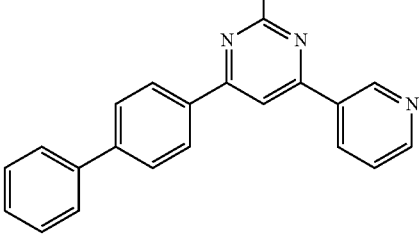

Example 22

An organic EL device was prepared in similar conditions to Example 20 except that the compound (Compound 27) according to Example 3 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-27) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 30)

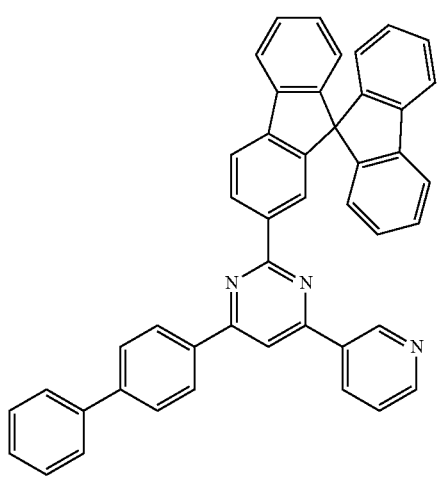

(Compound-27)

Example 23

An organic EL device was prepared in similar conditions to Example 20 except that the compound (Compound 36) according to Example 4 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-36) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 31)

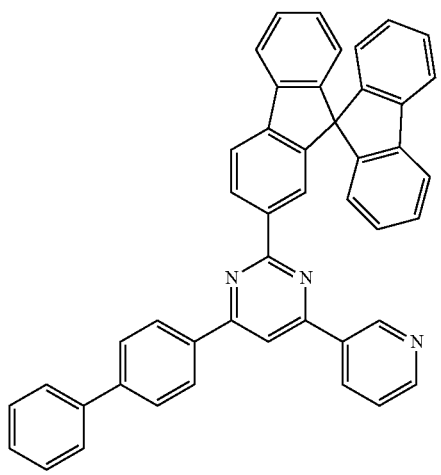

(Compound-36)

Example 24

An organic EL device was prepared in similar conditions to Example 20 except that the compound (Compound 43) according to Example 5 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-43) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 32)

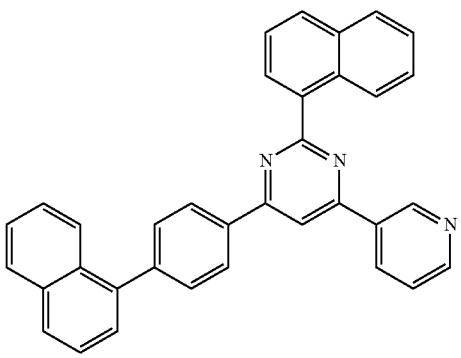

(Compound-43)

Example 25

An organic EL device was prepared in similar conditions to Example 20 except that the compound (Compound 46) according to Example 6 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-46) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 33)

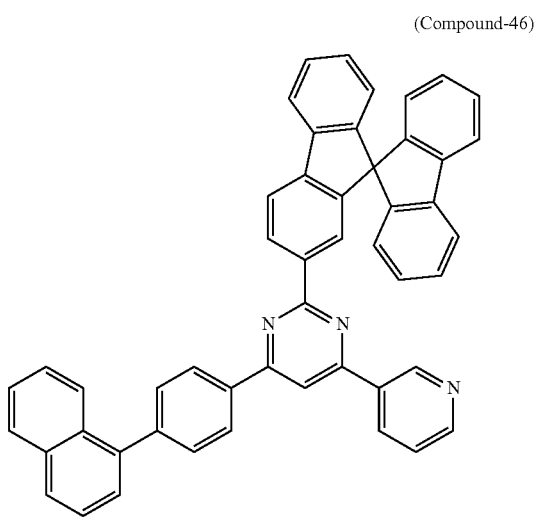

(Compound-46)

Example 26

An organic EL device was prepared in similar conditions to Example 20 except that the compound (Compound 149) according to Example 7 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-149) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 34)

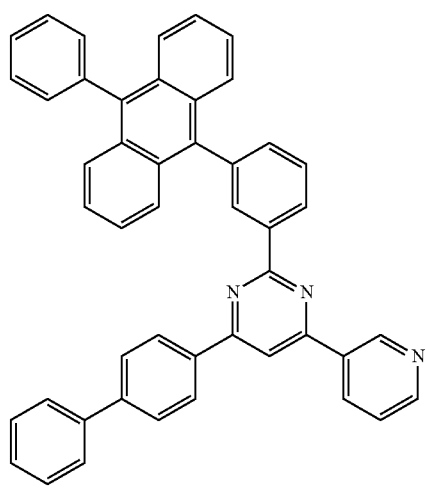

(Compound-149)

Example 27

An organic EL device was prepared in similar conditions to Example 20 except that the compound (Compound 151) according to Example 8 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-151) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 35)

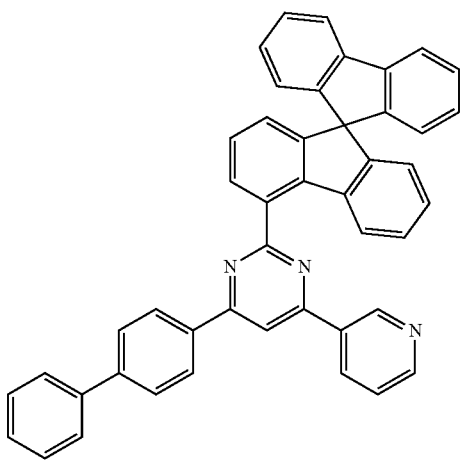

(Compound-151)

Example 28

An organic EL device was prepared in similar conditions to Example 20 except that the compound (Compound 152) according to Example 9 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-152) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 36)

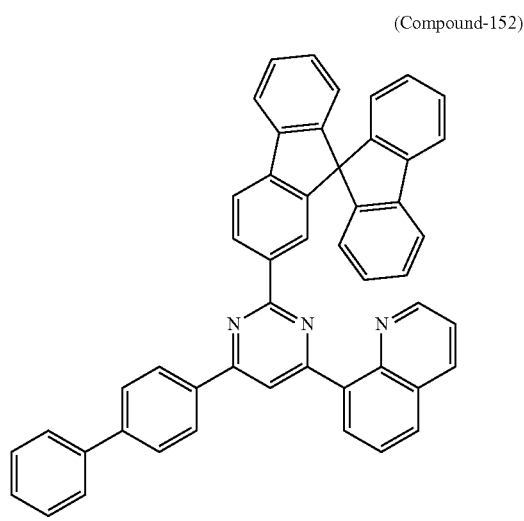

(Compound-152)

Example 29

An organic EL device was prepared in similar conditions to Example 20 except that the compound (Compound 153) according to Example 10 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-153) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 37)

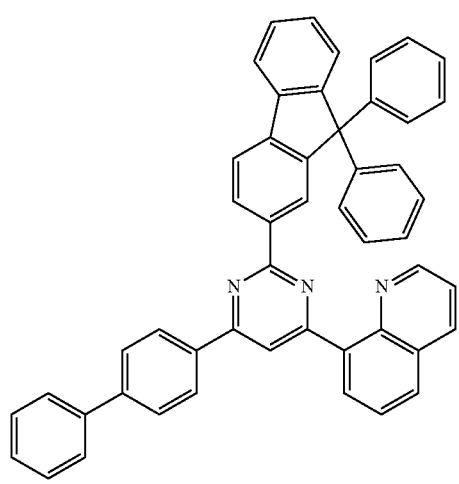

(Compound-153)

Example 30

An organic EL device was prepared in similar conditions to Example 20 except that the compound (Compound 154) according to Example 11 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-154) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 38)

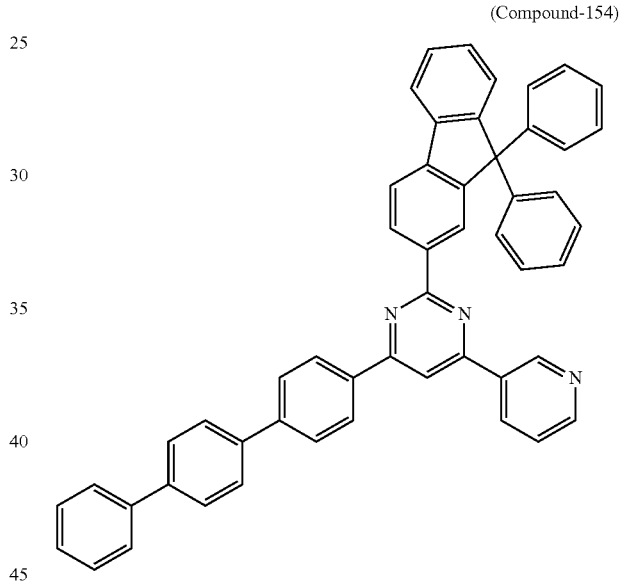

(Compound-154)

Example 31

An organic EL device was prepared in similar conditions to Example 20 except that the compound (Compound 155) according to Example 12 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-155) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 39)

(Compound-155)

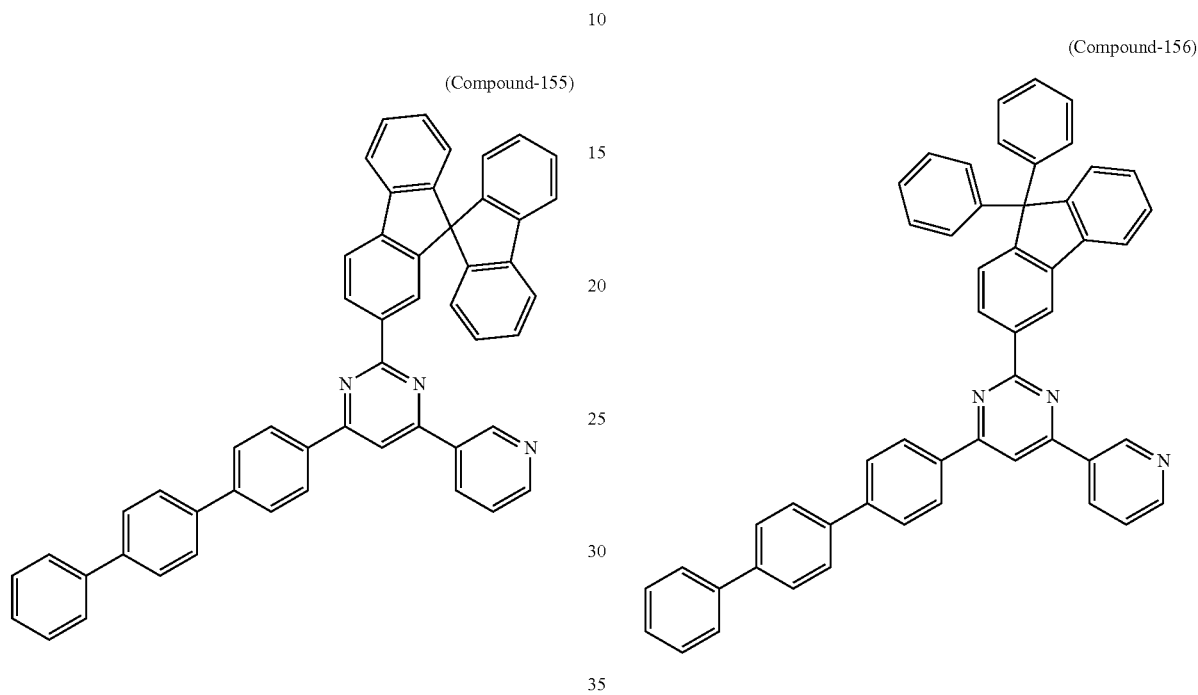

(Chem. 40)

(Compound-156)

Example 32

An organic EL device was prepared in similar conditions to Example 20 except that the compound (Compound 156) according to Example 13 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-156) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

Example 33

An organic EL device was prepared in similar conditions to Example 20 except that the compound (Compound 157) according to Example 14 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-157) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 41)

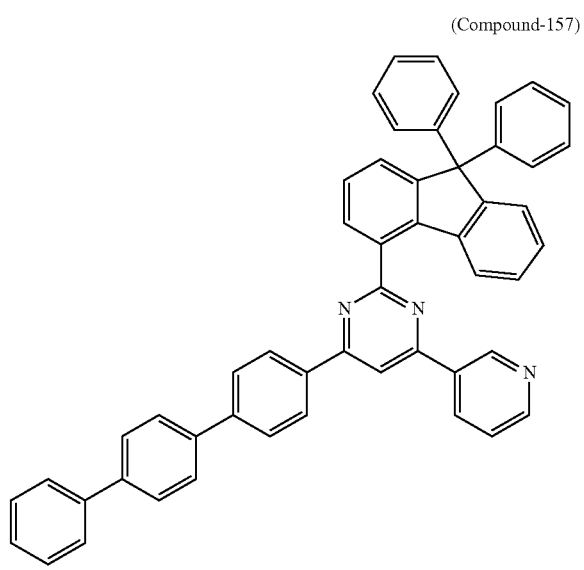
(Compound-157)

Example 34

An organic EL device was prepared in similar conditions to Example 20 except that the compound (Compound 158) according to Example 15 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-158) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 42)

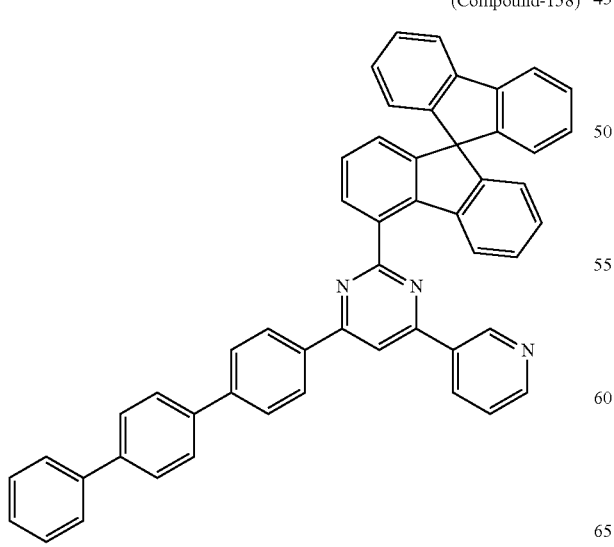
(Compound-158)

Example 35

An organic EL device was prepared in similar conditions to Example 20 except that the compound (Compound 159) according to Example 16 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-159) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 43)

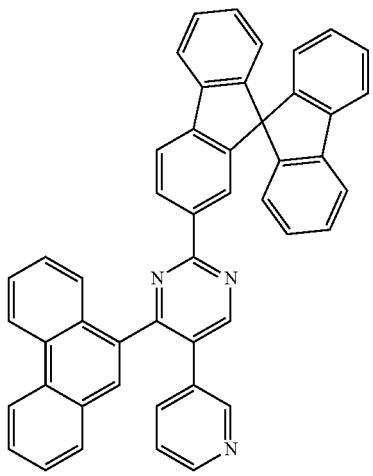
(Compound-159)

Example 36

An organic EL device was prepared in similar conditions to Example 20 except that the compound (Compound 160) according to Example 17 was used as the material of the hole blocking layer and electron transport layer 6 and 7 instead of the compound (Compound 17) according to Example 1 of the present invention and binary deposition was performed at a deposition rate in which the ratio of the deposition rates of the compound (Compound-160) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 44)

(Compound-160)

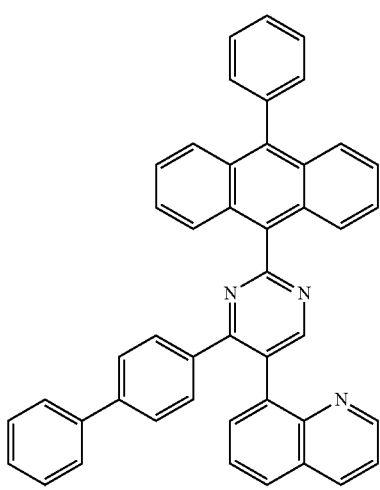

Comparative Example 1

For comparison, an organic EL device was prepared in similar conditions to Example 20 except that a compound (ETM-2) (see, for example, Patent Literature 6) having the following structural formula was used as the material of the hole blocking layer and electron transport layer 6 and 7 instead of the compound (Compound 17) according to Example 1 of the present invention and binary deposition was performed at a deposition rate in which the ratio of the deposition rates of the compound (ETM-2) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 45)

(ETM-2)

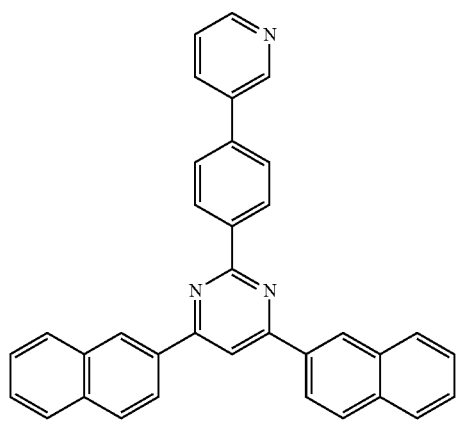

Comparative Example 2

For comparison, an organic EL device was prepared in similar conditions to Example 20 except that a compound (ETM-3) (see, for example, Patent Literature 8) having the following structural formula was used as the material of the hole blocking layer and electron transport layer 6 and 7 instead of the compound (Compound 17) according to Example 1 of the present invention and binary deposition was performed at a deposition rate in which the ratio of the deposition rates of the compound (ETM-3) and the compound (ETM-1) was 50:50. The characteristics of the prepared organic EL device were measured at room temperature in the atmosphere. The measurement results of the light-emitting characteristics when a direct current voltage was applied to the prepared organic EL device were collectively shown in Table 1.

(Chem. 46)

(ETM-3)

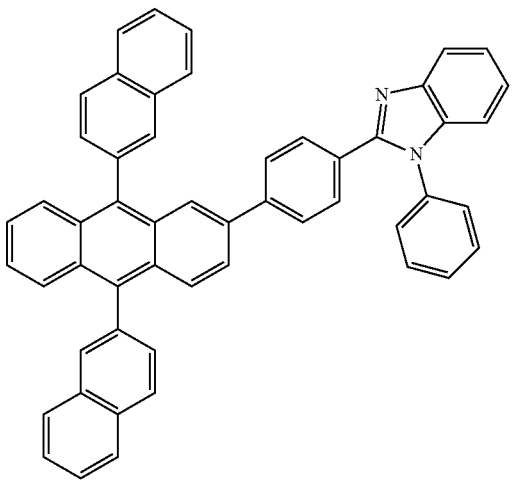

The device lifetime was measured using each of the organic EL devices prepared in Examples 20 to 36 and Comparative Examples 1 and 2, and the results were collectively shown in Table 1. The device lifetime was measured as the time until the light emission luminance attenuated to 1900 cd/m$^2$ (corresponding to 95% in the case where the initial luminance was 100%: 95% attenuation) when constant current driving was performed with the light emission luminance (initial luminance) at the start of light emission set to 2000 cd/m$^2$.

TABLE 1

|  | Hole blocking layer and electron transport layer | Voltage [V] (@10 mA/cm2) | Luminance [cd/m2] (@10 mA/cm2) | Light emission efficiency [cd/A] (@10 mA/cm2) | Power efficiency [lm/W] (@10 mA/cm2) | Element lifetime 95% attenuated |
|---|---|---|---|---|---|---|
| Example 20 | Compound-17/ETM-1 | 3.67 | 823 | 8.24 | 7.06 | 244 hours |
| Example 21 | Compound-26/ETM-1 | 3.56 | 895 | 8.95 | 7.89 | 231 hours |
| Example 22 | Compound-27/ETM-1 | 3.49 | 899 | 8.99 | 8.11 | 257 hours |
| Example 23 | Compound-36/ETM-1 | 3.60 | 887 | 8.87 | 7.74 | 307 hours |
| Example 24 | Compound-43/ETM-1 | 3.52 | 863 | 8.64 | 7.73 | 261 hours |
| Example 25 | Compound-46/ETM-1 | 3.49 | 887 | 8.88 | 8.00 | 287 hours |
| Example 26 | Compound-149/ETM-1 | 3.70 | 871 | 8.73 | 7.43 | 248 hours |
| Example 27 | Compound-151/ETM-1 | 3.42 | 861 | 8.61 | 7.90 | 252 hours |
| Example 28 | Compound-152/ETM-1 | 3.55 | 895 | 8.96 | 7.94 | 296 hours |
| Example 29 | Compound-153/ETM-1 | 3.56 | 873 | 8.74 | 7.73 | 283 hours |
| Example 30 | Compound-154/ETM-1 | 3.45 | 893 | 8.94 | 8.13 | 316 hours |
| Example 31 | Compound-155/ETM-1 | 3.45 | 887 | 8.88 | 8.09 | 259 hours |
| Example 32 | Compound-156/ETM-1 | 3.57 | 875 | 8.76 | 7.71 | 323 hours |
| Example 33 | Compound-157/ETM-1 | 3.72 | 873 | 8.75 | 7.40 | 271 hours |
| Example 34 | Compound-158/ETM-1 | 3.67 | 880 | 8.82 | 7.55 | 275 hours |
| Example 35 | Compound-159/ETM-1 | 3.44 | 923 | 9.24 | 8.43 | 233 hours |
| Example 36 | Compound-160/ETM-1 | 3.48 | 909 | 9.09 | 8.22 | 267 hours |
| Comparative Example 1 | ETM-2/ETM-1 | 3.82 | 805 | 8.05 | S.62 | 165 hours |
| Comparative Example 2 | ETM-3/ETM-1 | 4.01 | 659 | 6.59 | 5.16 | 203 hours |

As shown in Table 1, the drive voltage when a current having a current density of 10 mA/cm$^2$ was caused to flow was lowered to 3.42 to 3.72 V in the organic EL devices according to Examples 20 to 36 as compared with the 3.82 to 4.01 V of the organic EL devices according to Comparative Examples 1 and 2 using the compounds (ETM-2 and 3) having the above-mentioned structural formulae. Further, the light emission efficiency was improved to 8.24 to 9.24 cd/A in the organic EL devices according to Examples 20 to 36 as compared with 6.59 to 8.05 cd/A of the organic EL devices according to Comparative Examples 1 and 2. Also the power efficiency of the organic EL devices according to Examples 20 to 36 was largely improved to 7.06 to 8.43 lm/W as compared with 5.16 to 6.62 lm/W of the organic EL devices according to Comparative Examples 1 and 2. In particular, the device lifetime (95% attenuation) was largely extended to 231 to 323 hours in the organic EL devices according to Examples 20 to 36 as compared with 165 to 203 hours of the organic EL devices according to Comparative Examples 1 and 2.

As described above, the organic EL device according to the present invention is excellent in the light emission efficiency and power efficiency as compared with the devices using the compounds (ETM-2 and 3) having the above-mentioned structural formulae, and it has been found that it is possible to realize an organic EL device having a long lifetime.

INDUSTRIAL APPLICABILITY

The compound having a specific pyrimidine ring structure according to the present invention is excellent in electron injection property and hole blocking performance and is stable in a thin film state, and thus is suitably used as a compound for organic EL device. By preparing an organic EL device using the compound, it is possible to achieve high efficiency, reduce the drive voltage, and improve the durability. For example, it has become possible to expand to home appliances and lighting applications.

REFERENCE SIGNS LIST 1 glass substrate
2 transparent anode
3 hole injection layer
4 hole transport layer
5 light-emitting layer
6 hole blocking layer
7 electron transport layer
8 electron injection layer
9 cathode

The invention claimed is:

1. A compound having a pyrimidine ring structure, wherein
the compound having a pyrimidine ring structure is represented by the following general formula (4)

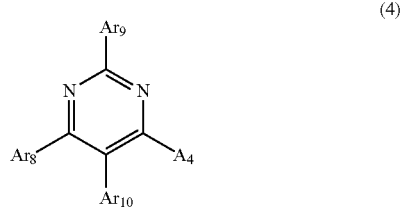

(4)

in the formula (4), $A_4$ represents a pyridyl group, or a quinolyl group, $Ar_8$ represents a substituted phenyl group, a substituted or unsubstituted biphenyl group, or a substituted or unsubstituted terphenyl group, the substituents thereof representing a phenyl group, a biphenyl group, or a naphthyl group, $Ar_9$ represents a substituted phenyl group, a substituted or unsubstituted fluorenyl group, or a substituted or unsubstituted spirobifluorenyl group, the substituents thereof representing a phenyl group, a phenanthrenyl group, or a spirobifluorenyl group, $Ar_{10}$ represents a hydrogen atom.

2. An organic electroluminescence device including a pair of electrodes and at least one organic layer sandwiched between the pair of electrodes, characterized in that
the compound having a pyrimidine ring structure according to claim 1 is used as a constituent material of the at least one organic material.

3. The organic electroluminescence device according to claim 2, wherein
the organic layer for which the compound having a pyrimidine ring structure is used is an electron transport layer.

4. The organic electroluminescence device according to claim 2, wherein
the organic layer for which the compound having a pyrimidine ring structure is used is a hole blocking layer.

5. The organic electroluminescence device according to claim 2, wherein
the organic layer for which the compound having a pyrimidine ring structure is used is a light-emitting layer.

6. The organic electroluminescence device according to claim 2, wherein
the organic layer for which the compound having a pyrimidine ring structure is used is an electron injection layer.

* * * * *